United States Patent
Altshuler et al.

(10) Patent No.: US 9,919,168 B2
(45) Date of Patent: Mar. 20, 2018

(54) METHOD FOR IMPROVEMENT OF CELLULITE APPEARANCE

(75) Inventors: Gregory B. Altshuler, Lincoln, MA (US); Henry H. Zenzie, Dover, MA (US); Christopher Gaal, Mansfield, MA (US); Richard Cohen, Sherborn, MA (US)

(73) Assignee: Palomar Medical Technologies, Inc., Burlington, MA (US)

( * ) Notice: Subject to any disclaimer, the term of this patent is extended or adjusted under 35 U.S.C. 154(b) by 1712 days.

(21) Appl. No.: 12/842,734

(22) Filed: Jul. 23, 2010

(65) Prior Publication Data

US 2011/0046523 A1 Feb. 24, 2011

Related U.S. Application Data

(60) Provisional application No. 61/271,593, filed on Jul. 23, 2009.

(51) Int. Cl.
| | | |
|---|---|---|
| *A61N 7/02* | (2006.01) | |
| *A61F 7/00* | (2006.01) | |
| *A61B 18/14* | (2006.01) | |
| *A61B 18/18* | (2006.01) | |
| *A61B 18/20* | (2006.01) | |
| *A61B 18/00* | (2006.01) | |
| *A61N 7/00* | (2006.01) | |
| *A61B 90/00* | (2016.01) | |

(52) U.S. Cl.
CPC .............. *A61N 7/02* (2013.01); *A61B 18/14* (2013.01); *A61B 18/1815* (2013.01); *A61B 18/20* (2013.01); *A61B 90/04* (2016.02); *A61B 2018/00023* (2013.01); *A61B 2090/378* (2016.02); *A61F 2007/0052* (2013.01); *A61N 2007/0008* (2013.01); *A61N 2007/0039* (2013.01)

(58) Field of Classification Search
USPC .......... 607/96–114; 601/6–14; 606/9–10, 27, 606/34, 31
See application file for complete search history.

(56) References Cited

U.S. PATENT DOCUMENTS

| | | |
|---|---|---|
| 853,033 A | 5/1907 | Roberts |
| 1,590,283 A | 6/1926 | Catlin |
| (Continued) | | |

FOREIGN PATENT DOCUMENTS

| | | |
|---|---|---|
| AT | 400305 | 4/1995 |
| AU | 1851583 A | 3/1984 |
| (Continued) | | |

OTHER PUBLICATIONS

US 6,230,044, 05/2001, Afanassieva et al. (withdrawn)
(Continued)

*Primary Examiner* — Joseph Stoklosa
*Assistant Examiner* — Adam Avigan
(74) *Attorney, Agent, or Firm* — Thomas J. Engellenner; Reza Mollaaghababa; Pepper Hamilton LLP

(57) ABSTRACT

A method and apparatus are provided for treating connective tissue. The method and apparatus includes elongating connective tissue including septa and/or fascia to achieve a lasting improvement (e.g., a long term, durable and/or substantially irreversible treatment of the connective tissue) to improve the appearance of cellulite.

14 Claims, 9 Drawing Sheets

(56) References Cited

U.S. PATENT DOCUMENTS

| | | |
|---|---|---|
| 1,706,161 A | 3/1929 | Hollnagen |
| 2,472,385 A | 6/1949 | Rollman |
| 2,669,771 A | 2/1954 | Burge et al. |
| 3,261,978 A | 7/1966 | Brenman |
| 3,327,712 A | 6/1967 | Kaufmann |
| 3,486,070 A | 12/1969 | Engel |
| 3,527,932 A | 9/1970 | Thomas |
| 3,538,919 A | 11/1970 | Meyer |
| 3,597,652 A | 8/1971 | Gates, Jr. |
| 3,622,743 A | 11/1971 | Muncheryan |
| 3,653,778 A | 4/1972 | Freiling |
| 3,667,454 A | 6/1972 | Prince |
| 3,693,623 A | 9/1972 | Harte et al. |
| 3,793,723 A | 2/1974 | Kuris et al. |
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,890,537 A | 6/1975 | Park et al. |
| 3,900,034 A | 8/1975 | Katz et al. |
| 3,909,649 A | 9/1975 | Arsena |
| 3,939,560 A | 2/1976 | Lyall |
| 3,977,083 A | 8/1976 | Leslie et al. |
| 4,047,106 A | 9/1977 | Robinson |
| 4,213,462 A | 7/1980 | Sato |
| 4,233,493 A | 11/1980 | Nath et al. |
| 4,254,333 A | 3/1981 | Bergstrom |
| 4,269,067 A | 5/1981 | Tynan et al. |
| 4,273,109 A | 6/1981 | Enderby |
| 4,275,335 A | 6/1981 | Ishida et al. |
| 4,298,005 A | 11/1981 | Mutzhas |
| 4,316,467 A | 2/1982 | Muckerheide |
| 4,333,197 A | 6/1982 | Kuris |
| 4,335,726 A | 6/1982 | Kolstedt |
| 4,388,924 A | 6/1983 | Weissman et al. |
| 4,409,479 A | 10/1983 | Sprague et al. |
| 4,452,081 A | 6/1984 | Seppi |
| 4,456,872 A | 6/1984 | Froeschle |
| 4,461,294 A | 7/1984 | Baron |
| 4,504,727 A | 3/1985 | Melcher et al. |
| 4,512,197 A | 4/1985 | von Gutfeld et al. |
| 4,524,289 A | 6/1985 | Hammond et al. |
| 4,539,987 A | 9/1985 | Nath et al. |
| 4,553,546 A | 11/1985 | Javelle |
| 4,561,440 A | 12/1985 | Kubo et al. |
| 4,566,271 A | 1/1986 | French et al. |
| 4,591,762 A | 5/1986 | Nakamura |
| 4,601,753 A | 7/1986 | Soileau et al. |
| 4,608,978 A | 9/1986 | Rohr |
| 4,608,979 A | 9/1986 | Breidenthal et al. |
| 4,617,926 A | 10/1986 | Sutton |
| 4,623,929 A | 11/1986 | Johnson et al. |
| 4,629,884 A | 12/1986 | Bergstrom |
| 4,653,495 A | 3/1987 | Nanaumi |
| 4,677,347 A | 6/1987 | Nakamura et al. |
| 4,686,986 A | 8/1987 | Fenyo et al. |
| 4,695,697 A | 9/1987 | Kosa |
| 4,710,677 A | 12/1987 | Halberstadt et al. |
| 4,718,416 A | 1/1988 | Nanaumi |
| 4,733,660 A | 3/1988 | Itzkan |
| 4,736,745 A | 4/1988 | Gluckman |
| 4,745,909 A | 5/1988 | Pelton et al. |
| 4,747,660 A | 5/1988 | Nishioka et al. |
| 4,749,913 A | 6/1988 | Stuermer et al. |
| 4,775,361 A | 10/1988 | Jacques et al. |
| 4,779,173 A | 10/1988 | Carr et al. |
| 4,784,135 A | 11/1988 | Blum et al. |
| 4,799,479 A | 1/1989 | Spears |
| 4,819,669 A | 4/1989 | Politzer |
| 4,826,431 A | 5/1989 | Fujimura et al. |
| 4,832,024 A | 5/1989 | Boussignac et al. |
| 4,840,174 A | 6/1989 | Gluckman |
| 4,840,563 A | 6/1989 | Altendorf |
| 4,845,608 A | 7/1989 | Gdula |
| 4,852,549 A | 8/1989 | Mori et al. |
| 4,860,172 A | 8/1989 | Schlager et al. |
| 4,860,744 A | 8/1989 | Johnson et al. |
| 4,862,903 A | 9/1989 | Campbell |
| 4,871,479 A | 10/1989 | Bachelard et al. |
| 4,884,560 A | 12/1989 | Kuracina |
| 4,898,438 A | 2/1990 | Mori |
| 4,905,690 A | 3/1990 | Ohshiro et al. |
| 4,914,298 A | 4/1990 | Quad et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,932,954 A | 6/1990 | Wondrazek et al. |
| 4,945,239 A | 7/1990 | Wist et al. |
| 4,973,848 A | 11/1990 | Kolobanov et al. |
| 4,976,308 A | 12/1990 | Faghri |
| 4,979,180 A | 12/1990 | Muncheryan |
| 4,992,256 A | 2/1991 | Skaggs et al. |
| 5,000,752 A | 3/1991 | Hoskin et al. |
| 5,030,090 A | 7/1991 | Maeda et al. |
| 5,032,178 A | 7/1991 | Cornell |
| 5,046,494 A | 9/1991 | Searfoss et al. |
| 5,050,597 A | 9/1991 | Daikuzono |
| 5,057,104 A | 10/1991 | Chess |
| 5,059,192 A | 10/1991 | Zaias |
| 5,065,515 A | 11/1991 | Iderosa |
| 5,066,293 A | 11/1991 | Furumoto |
| 5,071,417 A | 12/1991 | Sinofsky |
| 5,108,388 A | 4/1992 | Trokel |
| 5,127,395 A | 7/1992 | Bontemps |
| 5,133,102 A | 7/1992 | Sakuma et al. |
| 5,137,530 A | 8/1992 | Sand |
| 5,140,984 A | 8/1992 | Dew et al. |
| 5,159,601 A | 10/1992 | Huber |
| 5,160,194 A | 11/1992 | Feldman |
| 5,171,564 A | 12/1992 | Nathoo et al. |
| 5,178,617 A | 1/1993 | Kuizenga et al. |
| 5,182,557 A | 1/1993 | Lang |
| 5,182,857 A | 2/1993 | Simon |
| 5,192,278 A | 3/1993 | Hayes et al. |
| 5,196,004 A | 3/1993 | Sinofsky |
| 5,207,671 A | 5/1993 | Franken et al. |
| 5,222,907 A | 6/1993 | Katabuchi et al. |
| 5,225,926 A | 7/1993 | Cuomo et al. |
| 5,226,907 A | 7/1993 | Tankovich |
| 5,267,399 A | 12/1993 | Johnston |
| 5,281,211 A | 1/1994 | Parel et al. |
| 5,282,797 A | 2/1994 | Chess |
| 5,287,372 A | 2/1994 | Ortiz |
| 5,287,380 A | 2/1994 | Hsia |
| 5,293,880 A | 3/1994 | Levitt |
| 5,300,097 A | 4/1994 | Lerner et al. |
| 5,303,585 A | 4/1994 | Lichte |
| 5,304,170 A | 4/1994 | Green |
| 5,304,173 A | 4/1994 | Kittrell et al. |
| 5,306,143 A | 4/1994 | Levy |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,336,217 A | 8/1994 | Buys et al. |
| 5,342,358 A | 8/1994 | Daikuzono et al. |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,353,020 A | 10/1994 | Schurmann |
| 5,353,790 A | 10/1994 | Jacques et al. |
| 5,356,081 A | 10/1994 | Sellar |
| 5,358,503 A | 10/1994 | Bertwell et al. |
| 5,360,426 A | 11/1994 | Muller et al. |
| 5,369,831 A | 12/1994 | Bock |
| 5,380,317 A | 1/1995 | Everett et al. |
| 5,386,427 A | 1/1995 | Zayhowski |
| 5,403,306 A | 4/1995 | Edwards et al. |
| 5,405,368 A | 4/1995 | Eckhouse |
| 5,409,446 A | 4/1995 | Rattner |
| 5,415,654 A | 5/1995 | Daikuzono |
| 5,422,112 A | 6/1995 | Williams |

(56) References Cited

U.S. PATENT DOCUMENTS

| | | |
|---|---|---|
| 5,425,728 A | 6/1995 | Tankovich |
| 5,425,735 A | 6/1995 | Rosen et al. |
| 5,425,754 A | 6/1995 | Braun et al. |
| 5,445,608 A | 8/1995 | Chen et al. |
| 5,445,611 A | 8/1995 | Eppstein et al. |
| 5,454,807 A | 10/1995 | Lennox et al. |
| 5,458,140 A | 10/1995 | Eppstein et al. |
| 5,474,549 A | 12/1995 | Ortiz et al. |
| 5,486,170 A | 1/1996 | Winston et al. |
| 5,486,172 A | 1/1996 | Chess |
| 5,501,680 A | 3/1996 | Kurtz et al. |
| 5,502,582 A | 3/1996 | Larson et al. |
| 5,505,726 A | 4/1996 | Meserol |
| 5,505,727 A | 4/1996 | Keller |
| 5,519,534 A | 5/1996 | Smith et al. |
| 5,522,813 A | 6/1996 | Trelles |
| 5,527,368 A | 6/1996 | Supkis et al. |
| 5,531,739 A | 7/1996 | Trelles |
| 5,531,740 A | 7/1996 | Black |
| 5,536,168 A | 7/1996 | Bourke et al. |
| 5,549,660 A | 8/1996 | Mendes et al. |
| 5,558,667 A | 9/1996 | Yarborough et al. |
| 5,561,881 A | 10/1996 | Klinger et al. |
| 5,571,098 A | 11/1996 | Domankevitz et al. |
| 5,578,866 A | 11/1996 | DePoorter et al. |
| 5,595,568 A | 1/1997 | Anderson et al. |
| 5,611,793 A | 3/1997 | Wilson et al. |
| 5,616,140 A | 4/1997 | Prescott |
| 5,618,284 A | 4/1997 | Sand |
| 5,620,478 A | 4/1997 | Eckhouse et al. |
| 5,626,631 A | 5/1997 | Eckhouse et al. |
| 5,628,744 A | 5/1997 | Coleman et al. |
| 5,630,811 A | 5/1997 | Miller |
| 5,634,711 A | 6/1997 | Kennedy et al. |
| 5,649,972 A | 7/1997 | Hochstein |
| 5,652,481 A | 7/1997 | Johnson et al. |
| 5,653,706 A | 8/1997 | Zavislan et al. |
| 5,655,547 A | 8/1997 | Karni |
| 5,657,760 A | 8/1997 | Ying et al. |
| 5,658,148 A | 8/1997 | Neuberger et al. |
| 5,658,323 A | 8/1997 | Miller |
| 5,660,836 A | 8/1997 | Knowlton |
| 5,661,744 A | 8/1997 | Murakami et al. |
| 5,662,643 A | 9/1997 | Kung et al. |
| 5,662,644 A | 9/1997 | Swor |
| 5,673,451 A | 10/1997 | Moore et al. |
| 5,679,113 A | 10/1997 | Caisey et al. |
| 5,683,380 A | 11/1997 | Eckhouse et al. |
| 5,692,509 A | 12/1997 | Voss et al. |
| 5,698,866 A | 12/1997 | Doiron et al. |
| 5,707,401 A | 1/1998 | Martin et al. |
| 5,707,403 A | 1/1998 | Grove et al. |
| 5,713,738 A | 2/1998 | Yarborough |
| 5,714,119 A | 2/1998 | Kawagoe et al. |
| 5,720,772 A | 2/1998 | Eckhouse |
| 5,722,397 A | 3/1998 | Eppstein |
| 5,725,522 A | 3/1998 | Sinofsky |
| 5,728,090 A | 3/1998 | Martin et al. |
| 5,735,844 A | 4/1998 | Anderson et al. |
| 5,735,884 A | 4/1998 | Thompson et al. |
| 5,738,678 A | 4/1998 | Patel |
| 5,742,392 A | 4/1998 | Anderson et al. |
| 5,743,901 A | 4/1998 | Grove et al. |
| 5,743,902 A | 4/1998 | Trost |
| 5,746,735 A | 5/1998 | Furumoto et al. |
| 5,748,822 A | 5/1998 | Miura et al. |
| 5,755,751 A | 5/1998 | Eckhouse |
| 5,759,200 A | 6/1998 | Azar |
| 5,760,362 A | 6/1998 | Eloy |
| 5,769,076 A | 6/1998 | Maekawa et al. |
| 5,782,249 A | 7/1998 | Weber et al. |
| 5,802,136 A | 9/1998 | Carol |
| 5,810,801 A | 9/1998 | Anderson et al. |
| 5,812,567 A | 9/1998 | Jeon et al. |
| 5,813,855 A | 9/1998 | Crisio, Jr. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,827,264 A | 10/1998 | Hohla |
| 5,828,803 A | 10/1998 | Eckhouse |
| 5,830,208 A | 11/1998 | Muller |
| 5,835,648 A | 11/1998 | Narciso, Jr. et al. |
| 5,836,877 A | 11/1998 | Zavislan |
| 5,836,999 A | 11/1998 | Eckhouse et al. |
| 5,840,048 A | 11/1998 | Cheng |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,868,732 A | 2/1999 | Waldman et al. |
| 5,871,480 A | 2/1999 | Tankovich |
| 5,879,159 A | 3/1999 | Cipolla |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A | 4/1999 | Uram |
| 5,895,350 A | 4/1999 | Hori |
| 5,897,549 A | 4/1999 | Tankovich |
| 5,906,609 A | 5/1999 | Assa et al. |
| 5,908,418 A | 6/1999 | Dority et al. |
| 5,913,883 A | 6/1999 | Alexander et al. |
| 5,916,211 A | 6/1999 | Quon et al. |
| 5,920,374 A | 7/1999 | Vaphiades et al. |
| 5,921,926 A | 7/1999 | Rolland et al. |
| 5,928,222 A | 7/1999 | Kleinerman |
| 5,944,687 A | 8/1999 | Benett et al. |
| 5,944,748 A | 8/1999 | Mager et al. |
| 5,948,011 A | 9/1999 | Knowlton |
| 5,949,222 A | 9/1999 | Buono |
| 5,954,710 A | 9/1999 | Paolini et al. |
| 5,955,490 A | 9/1999 | Kennedy et al. |
| 5,957,915 A | 9/1999 | Trost |
| 5,964,749 A | 10/1999 | Eckhouse et al. |
| 5,968,033 A | 10/1999 | Fuller et al. |
| 5,968,034 A | 10/1999 | Fullmer et al. |
| 5,974,059 A | 10/1999 | Dawson |
| 5,974,616 A | 11/1999 | Dreyfus |
| 5,977,723 A | 11/1999 | Yoon |
| 5,979,454 A | 11/1999 | Anvari et al. |
| 5,984,915 A | 11/1999 | Loeb et al. |
| 6,007,219 A | 12/1999 | O'Meara |
| 6,015,404 A | 1/2000 | Altshuler et al. |
| 6,022,316 A | 2/2000 | Eppstein et al. |
| 6,024,095 A * | 2/2000 | Stanley, III .................. 128/898 |
| 6,026,828 A | 2/2000 | Altshuler |
| 6,027,495 A | 2/2000 | Miller |
| 6,029,303 A | 2/2000 | Dewan |
| 6,029,304 A | 2/2000 | Hulke et al. |
| 6,030,378 A | 2/2000 | Stewart |
| 6,030,399 A | 2/2000 | Ignotz et al. |
| 6,032,071 A | 2/2000 | Binder |
| RE36,634 E | 3/2000 | Ghaffari |
| 6,036,684 A | 3/2000 | Tankovich et al. |
| 6,044,514 A | 4/2000 | Kaneda et al. |
| 6,050,990 A | 4/2000 | Tankovich et al. |
| D424,197 S | 5/2000 | Sydlowski et al. |
| 6,056,548 A | 5/2000 | Neuberger et al. |
| 6,056,738 A | 5/2000 | Marchitto et al. |
| 6,058,937 A | 5/2000 | Doiron et al. |
| 6,059,820 A | 5/2000 | Baronov |
| 6,063,108 A | 5/2000 | Salansky et al. |
| 6,070,092 A | 5/2000 | Kazama et al. |
| 6,071,239 A | 6/2000 | Cribbs et al. |
| 6,074,382 A | 6/2000 | Asah et al. |
| 6,080,146 A | 6/2000 | Altshuler et al. |
| 6,080,147 A | 6/2000 | Tobinick |
| 6,083,217 A | 7/2000 | Tankovich |

(56) References Cited

U.S. PATENT DOCUMENTS

| | | |
|---|---|---|
| 6,086,363 A | 7/2000 | Moran et al. |
| 6,086,580 A | 7/2000 | Mordon et al. |
| 6,094,767 A | 8/2000 | Iimura |
| 6,096,029 A | 8/2000 | O'Donnell, Jr. |
| 6,096,209 A | 8/2000 | O'Brien et al. |
| 6,099,521 A | 8/2000 | Shadduck |
| 6,104,959 A | 8/2000 | Spertell |
| 6,106,293 A | 8/2000 | Wiesel |
| 6,106,294 A | 8/2000 | Daniel |
| 6,110,195 A | 8/2000 | Xie et al. |
| 6,113,559 A | 9/2000 | Klopotek |
| 6,117,129 A | 9/2000 | Mukai |
| 6,120,497 A | 9/2000 | Anderson et al. |
| 6,126,655 A | 10/2000 | Domankevitz et al. |
| 6,129,723 A | 10/2000 | Anderson et al. |
| 6,135,774 A | 10/2000 | Hack et al. |
| 6,142,650 A | 11/2000 | Brown et al. |
| 6,142,939 A | 11/2000 | Eppstein et al. |
| 6,149,644 A | 11/2000 | Xie |
| 6,149,895 A | 11/2000 | Kutsch |
| 6,159,236 A | 12/2000 | Biel |
| 6,162,055 A | 12/2000 | Montgomery et al. |
| 6,162,211 A | 12/2000 | Tankovich et al. |
| 6,162,212 A | 12/2000 | Kreindel et al. |
| 6,171,300 B1 | 1/2001 | Adams |
| 6,171,301 B1 | 1/2001 | Nelson |
| 6,171,302 B1 | 1/2001 | Talpalriu et al. |
| 6,171,332 B1 | 1/2001 | Whitehurst |
| 6,173,202 B1 | 1/2001 | Eppstein |
| 6,174,325 B1 | 1/2001 | Eckhouse |
| 6,176,854 B1 | 1/2001 | Cone |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,187,029 B1 | 2/2001 | Shapiro et al. |
| 6,197,020 B1 | 3/2001 | O'Donnell, Jr. |
| 6,200,134 B1 | 3/2001 | Kovac et al. |
| 6,200,309 B1 | 3/2001 | Rice et al. |
| 6,202,242 B1 | 3/2001 | Salmon et al. |
| 6,203,540 B1 | 3/2001 | Weber |
| 6,210,425 B1 | 4/2001 | Chen |
| 6,214,034 B1 | 4/2001 | Azar |
| 6,221,068 B1 | 4/2001 | Fried et al. |
| 6,221,095 B1 | 4/2001 | Van Zuylen et al. |
| 6,228,075 B1 | 5/2001 | Furumoto |
| 6,229,831 B1 | 5/2001 | Nightingale et al. |
| 6,235,015 B1 | 5/2001 | Mead, III et al. |
| 6,235,016 B1 | 5/2001 | Stewart |
| 6,236,891 B1 | 5/2001 | Ingle et al. |
| 6,239,442 B1 | 5/2001 | Iimura et al. |
| 6,240,306 B1 | 5/2001 | Rohrscheib et al. |
| 6,245,093 B1 | 6/2001 | Li et al. |
| 6,251,127 B1 | 6/2001 | Biel |
| 6,254,388 B1 | 7/2001 | Yarborough |
| 6,263,233 B1 | 7/2001 | Zavislan et al. |
| 6,264,649 B1 | 7/2001 | Whitcroft et al. |
| 6,267,779 B1 | 7/2001 | Gerdes |
| 6,267,780 B1 | 7/2001 | Streeter |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,283,956 B1 | 9/2001 | McDaniel |
| 6,287,549 B1 | 9/2001 | Sumian et al. |
| 6,290,496 B1 | 9/2001 | Azar et al. |
| 6,290,713 B1 | 9/2001 | Russell |
| 6,306,130 B1 | 10/2001 | Anderson et al. |
| 6,306,160 B1 | 10/2001 | Nidetzky |
| 6,315,772 B1 | 11/2001 | Marchitto et al. |
| 6,317,624 B1 | 11/2001 | Kollias et al. |
| 6,319,274 B1 | 11/2001 | Shadduck |
| 6,325,769 B1 | 12/2001 | Klopotek |
| 6,328,733 B1 | 12/2001 | Trost |
| 6,331,111 B1 | 12/2001 | Cao |
| 6,340,495 B1 | 1/2002 | Sumian et al. |
| 6,343,400 B1 | 2/2002 | Massholder et al. |
| 6,343,933 B1 | 2/2002 | Montgomery et al. |
| 6,350,261 B1 | 2/2002 | Domankevitz et al. |
| 6,350,276 B1 | 2/2002 | Knowlton |
| 6,354,370 B1 | 3/2002 | Miller et al. |
| 6,355,054 B1 | 3/2002 | Neuberger et al. |
| 6,358,242 B1 | 3/2002 | Cecchetti |
| 6,358,272 B1 | 3/2002 | Wilden |
| 6,383,176 B1 | 5/2002 | Connors et al. |
| 6,383,177 B1 | 5/2002 | Balle-Petersen et al. |
| 6,387,089 B1 | 5/2002 | Kreindel et al. |
| 6,387,353 B1 | 5/2002 | Jensen et al. |
| 6,395,016 B1 | 5/2002 | Oron et al. |
| 6,400,011 B1 | 6/2002 | Miki |
| 6,402,739 B1 | 6/2002 | Neev |
| 6,406,474 B1 | 6/2002 | Neuberger et al. |
| 6,409,665 B1 | 6/2002 | Scott et al. |
| 6,413,267 B1 | 7/2002 | Dumoulin-White et al. |
| 6,416,319 B1 | 7/2002 | Cipolla |
| 6,419,389 B1 | 7/2002 | Fuchs et al. |
| 6,424,852 B1 | 7/2002 | Zavislan |
| 6,425,912 B1 | 7/2002 | Knowlton |
| 6,435,873 B1 | 8/2002 | Burgio |
| 6,436,094 B1 | 8/2002 | Reuter |
| 6,439,888 B1 | 8/2002 | Boutoussov et al. |
| 6,440,155 B1 | 8/2002 | Matsumae et al. |
| 6,443,978 B1 | 9/2002 | Zharov |
| 6,451,007 B1 | 9/2002 | Koop et al. |
| 6,461,296 B1 | 10/2002 | Desai |
| 6,464,694 B1 | 10/2002 | Massengill |
| 6,471,712 B2 | 10/2002 | Burres |
| 6,471,716 B1 | 10/2002 | Pecukonis |
| 6,475,211 B2 | 11/2002 | Chess et al. |
| 6,484,052 B1 | 11/2002 | Visuri et al. |
| 6,485,413 B1 | 11/2002 | Boppart et al. |
| 6,491,685 B2 | 12/2002 | Visuri et al. |
| 6,494,900 B1 | 12/2002 | Salansky et al. |
| 6,497,702 B1 | 12/2002 | Bernaz |
| 6,503,486 B2 | 1/2003 | Xu et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,519,376 B2 | 2/2003 | Biagi et al. |
| 6,525,819 B1 | 2/2003 | Delawter et al. |
| 6,527,716 B1 | 3/2003 | Eppstein |
| 6,527,764 B1 | 3/2003 | Neuberger et al. |
| 6,530,915 B1 | 3/2003 | Eppstein et al. |
| 6,537,270 B1 | 3/2003 | Elbrecht et al. |
| 6,547,780 B1 | 4/2003 | Sinofsky |
| 6,551,346 B2 | 4/2003 | Crossley |
| 6,554,439 B1 | 4/2003 | Teicher et al. |
| 6,556,596 B1 | 4/2003 | Kim et al. |
| 6,558,372 B1 | 5/2003 | Altshuler |
| 6,561,808 B2 | 5/2003 | Neuberger et al. |
| 6,569,155 B1 | 5/2003 | Connors et al. |
| 6,570,892 B1 | 5/2003 | Lin et al. |
| 6,570,893 B1 | 5/2003 | Libatique et al. |
| 6,572,634 B2 | 6/2003 | Koo |
| 6,572,637 B1 | 6/2003 | Yamazaki et al. |
| 6,595,934 B1 | 7/2003 | Hissong et al. |
| 6,600,951 B1 | 7/2003 | Anderson |
| 6,602,245 B1 | 8/2003 | Thiberg |
| 6,605,080 B1 | 8/2003 | Altshuler et al. |
| 6,605,083 B2 | 8/2003 | Clement et al. |
| 6,606,755 B1 | 8/2003 | Robinson et al. |
| 6,616,447 B1 | 9/2003 | Rizoiu et al. |
| 6,616,451 B1 | 9/2003 | Rizolu et al. |
| 6,618,531 B1 | 9/2003 | Goto et al. |
| 6,623,272 B2 | 9/2003 | Clemans |
| 6,623,513 B2 | 9/2003 | Biel |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |

(56) References Cited

U.S. PATENT DOCUMENTS

| | | |
|---|---|---|
| 6,652,459 B2 | 11/2003 | Payne et al. |
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,675,425 B1 | 1/2004 | Iimura et al. |
| 6,676,654 B1 | 1/2004 | Balle-Petersen et al. |
| 6,679,837 B2 | 1/2004 | Daikuzono |
| 6,685,639 B1 | 2/2004 | Wang et al. |
| 6,685,699 B1 | 2/2004 | Eppstein et al. |
| 6,689,124 B1 | 2/2004 | Thiberg |
| 6,692,456 B1 | 2/2004 | Eppstein et al. |
| 6,699,040 B1 | 3/2004 | Hahn et al. |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,743,222 B2 | 6/2004 | Durkin et al. |
| 6,746,444 B2 | 6/2004 | Key |
| 6,749,623 B1 | 6/2004 | Hsi et al. |
| 6,770,069 B1 | 8/2004 | Hobart et al. |
| 6,790,205 B1 | 9/2004 | Yamazaki et al. |
| 6,801,595 B2 | 10/2004 | Grodzins et al. |
| 6,808,331 B2 | 10/2004 | Hall et al. |
| 6,808,532 B2 | 10/2004 | Andersen et al. |
| RE38,670 E | 12/2004 | Asah et al. |
| 6,858,009 B2 | 2/2005 | Kawata et al. |
| 6,860,879 B2 | 3/2005 | Irion et al. |
| 6,862,771 B1 | 3/2005 | Muller |
| 6,863,781 B2 | 3/2005 | Nocera et al. |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 6,893,259 B1 | 5/2005 | Reizenson |
| 6,902,397 B2 | 6/2005 | Farrell et al. |
| 6,902,563 B2 | 6/2005 | Wilkens et al. |
| 6,936,046 B2 | 8/2005 | Hissong et al. |
| 6,942,658 B1 | 9/2005 | Rizoiu et al. |
| 6,953,341 B2 | 10/2005 | Black |
| 6,974,451 B2 | 12/2005 | Altshuler et al. |
| 6,976,985 B2 | 12/2005 | Altshuler et al. |
| 6,989,023 B2 | 1/2006 | Black |
| 6,991,644 B2 | 1/2006 | Spooner et al. |
| 6,997,923 B2 | 2/2006 | Anderson et al. |
| 7,001,413 B2 | 2/2006 | Butler |
| 7,006,223 B2 | 2/2006 | Mullani |
| 7,029,469 B2 | 4/2006 | Vasily |
| 7,033,349 B2 | 4/2006 | Key |
| 7,041,100 B2 | 5/2006 | Kreindel |
| 7,044,959 B2 | 5/2006 | Anderson et al. |
| 7,060,061 B2 | 6/2006 | Altshuler et al. |
| 7,066,733 B2 | 6/2006 | Logan et al. |
| 7,070,611 B2 | 7/2006 | Biel |
| 7,077,840 B2 | 7/2006 | Altshuler et al. |
| 7,081,128 B2 | 7/2006 | Hart et al. |
| 7,097,639 B1 | 8/2006 | Almeida |
| 7,097,656 B1 | 8/2006 | Akopov et al. |
| 7,135,033 B2 | 11/2006 | Altshuler et al. |
| 7,144,247 B2 | 12/2006 | Black |
| 7,144,248 B2 | 12/2006 | Irwin |
| 7,145,105 B2 | 12/2006 | Gaulard |
| 7,145,108 B2 | 12/2006 | Kanel et al. |
| 7,160,289 B2 | 1/2007 | Cohen |
| 7,182,760 B2 | 2/2007 | Kubota |
| 7,198,634 B2 | 4/2007 | Harth et al. |
| 7,204,832 B2 | 4/2007 | Altshuler et al. |
| 7,220,254 B2 | 5/2007 | Altshuler et al. |
| 7,223,270 B2 | 5/2007 | Altshuler et al. |
| 7,223,281 B2 | 5/2007 | Altshuler et al. |
| 7,255,691 B2 | 8/2007 | Tolkoff et al. |
| 7,274,155 B2 | 9/2007 | Inochkin et al. |
| 7,276,058 B2 | 10/2007 | Altshuler et al. |
| 7,291,140 B2 | 11/2007 | MacFarland et al. |
| 7,291,141 B2 | 11/2007 | Jay |
| 7,309,335 B2 | 12/2007 | Altshuler et al. |
| 7,311,722 B2 | 12/2007 | Larsen |
| 7,322,972 B2 | 1/2008 | Viator et al. |
| 7,329,273 B2 | 2/2008 | Altshuler et al. |
| 7,329,274 B2 | 2/2008 | Altshuler et al. |
| 7,331,953 B2 | 2/2008 | Manstein et al. |
| 7,331,964 B2 | 2/2008 | Maricle et al. |
| 7,333,698 B2 | 2/2008 | Israel |
| 7,351,252 B2 | 4/2008 | Altshuler et al. |
| 7,422,598 B2 | 9/2008 | Altshuler et al. |
| 7,423,767 B2 | 9/2008 | Steinsiek et al. |
| 7,431,719 B2 | 10/2008 | Altshuler et al. |
| 7,531,967 B2 | 5/2009 | Inochkin et al. |
| 7,540,869 B2 | 6/2009 | Altshuler et al. |
| 7,624,640 B2 | 12/2009 | Maris et al. |
| 7,647,092 B2 | 1/2010 | Motz et al. |
| 7,758,621 B2 | 7/2010 | Altshuler et al. |
| 7,763,016 B2 | 7/2010 | Altshuler et al. |
| 7,935,107 B2 | 5/2011 | Altshuler et al. |
| 7,938,821 B2 | 5/2011 | Chan et al. |
| 7,942,915 B2 | 5/2011 | Altshuler et al. |
| 7,942,916 B2 | 5/2011 | Altshuler et al. |
| 8,002,768 B1 | 8/2011 | Altshuler et al. |
| 2001/0007068 A1 | 7/2001 | Ota et al. |
| 2001/0008973 A1 | 7/2001 | Van Zuylen et al. |
| 2001/0016732 A1 | 8/2001 | Hobart et al. |
| 2001/0023363 A1 | 9/2001 | Harth et al. |
| 2001/0024777 A1 | 9/2001 | Azar et al. |
| 2001/0025173 A1 | 9/2001 | Ritchie et al. |
| 2001/0041886 A1 | 11/2001 | Durkin et al. |
| 2001/0046652 A1 | 11/2001 | Ostler et al. |
| 2001/0048077 A1 | 12/2001 | Afanassieva |
| 2002/0004066 A1 | 1/2002 | Stanley et al. |
| 2002/0005475 A1 | 1/2002 | Zenzie |
| 2002/0013572 A1 | 1/2002 | Berlin |
| 2002/0016587 A1 | 2/2002 | Furumoto |
| 2002/0018754 A1 | 2/2002 | Sagel et al. |
| 2002/0019624 A1 | 2/2002 | Clement et al. |
| 2002/0026225 A1 | 2/2002 | Segal |
| 2002/0029071 A1 | 3/2002 | Whitehurst |
| 2002/0049483 A1 | 4/2002 | Knowlton |
| 2002/0058890 A1 | 5/2002 | Visuri et al. |
| 2002/0071287 A1 | 6/2002 | Haase |
| 2002/0071827 A1 | 6/2002 | Petersen et al. |
| 2002/0072676 A1 | 6/2002 | Afanassieva |
| 2002/0081555 A1 | 6/2002 | Wiesel |
| 2002/0090725 A1 | 7/2002 | Simpson et al. |
| 2002/0091377 A1 | 7/2002 | Anderson et al. |
| 2002/0108193 A1 | 8/2002 | Gruber |
| 2002/0111610 A1 | 8/2002 | Nordquist |
| 2002/0120256 A1 | 8/2002 | Furuno et al. |
| 2002/0123745 A1 | 9/2002 | Svaasand et al. |
| 2002/0127224 A1 | 9/2002 | Chen |
| 2002/0128635 A1 | 9/2002 | Altshuler et al. |
| 2002/0128695 A1 | 9/2002 | Harth et al. |
| 2002/0161357 A1 | 10/2002 | Anderson et al. |
| 2002/0161418 A1 | 10/2002 | Wilkens et al. |
| 2002/0173780 A1 | 11/2002 | Altshuler et al. |
| 2002/0182563 A1 | 12/2002 | Boutoussov et al. |
| 2002/0183808 A1 | 12/2002 | Biel |
| 2002/0198517 A1 | 12/2002 | Alfano et al. |
| 2003/0004499 A1 | 1/2003 | McDaniel |
| 2003/0009158 A1 | 1/2003 | Perricone |
| 2003/0009205 A1 | 1/2003 | Biel |
| 2003/0018373 A1 | 1/2003 | Eckhardt et al. |
| 2003/0023235 A1 | 1/2003 | Cense et al. |
| 2003/0023283 A1 | 1/2003 | McDaniel |
| 2003/0023284 A1 | 1/2003 | Gartstein et al. |
| 2003/0028227 A1 | 2/2003 | Neuberger et al. |
| 2003/0032900 A1 | 2/2003 | Ella |
| 2003/0032950 A1 | 2/2003 | Altshuler et al. |
| 2003/0036680 A1 | 2/2003 | Black |
| 2003/0040739 A1 | 2/2003 | Koop |
| 2003/0055414 A1 | 3/2003 | Altshuler et al. |
| 2003/0057875 A1 | 3/2003 | Inochkin et al. |
| 2003/0059738 A1 | 3/2003 | Neuberger |
| 2003/0065314 A1 | 4/2003 | Altshuler et al. |

(56) References Cited

U.S. PATENT DOCUMENTS

| | | |
|---|---|---|
| 2003/0083649 A1 | 5/2003 | Margaron et al. |
| 2003/0084534 A1 | 5/2003 | Kaizuka |
| 2003/0097122 A1 | 5/2003 | Ganz et al. |
| 2003/0100936 A1 | 5/2003 | Altshuler et al. |
| 2003/0104340 A1 | 6/2003 | Clemans |
| 2003/0109787 A1 | 6/2003 | Black |
| 2003/0109860 A1 | 6/2003 | Black |
| 2003/0113684 A1 | 6/2003 | Scott |
| 2003/0129154 A1 | 7/2003 | McDaniel |
| 2003/0130709 A1 | 7/2003 | D.C. et al. |
| 2003/0152528 A1 | 8/2003 | Singh et al. |
| 2003/0163884 A1 | 9/2003 | Weihrauch |
| 2003/0167080 A1 | 9/2003 | Hart et al. |
| 2003/0169433 A1 | 9/2003 | Koele et al. |
| 2003/0181896 A1 | 9/2003 | Zvuloni et al. |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0216719 A1 | 11/2003 | Debenedictis et al. |
| 2003/0216795 A1 | 11/2003 | Harth et al. |
| 2003/0232303 A1 | 12/2003 | Black |
| 2004/0006332 A1 | 1/2004 | Black |
| 2004/0010298 A1 | 1/2004 | Altshuler et al. |
| 2004/0015156 A1 | 1/2004 | Vasily |
| 2004/0015158 A1 | 1/2004 | Chen et al. |
| 2004/0019120 A1 | 1/2004 | Vargas et al. |
| 2004/0019990 A1 | 2/2004 | Farrell et al. |
| 2004/0024388 A1 | 2/2004 | Altshuler |
| 2004/0024430 A1 | 2/2004 | Bader et al. |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0092506 A1 | 5/2004 | Thompson et al. |
| 2004/0093042 A1 | 5/2004 | Altshuler et al. |
| 2004/0093043 A1 | 5/2004 | Edel et al. |
| 2004/0111132 A1 | 6/2004 | Shenderova et al. |
| 2004/0116984 A1 | 6/2004 | Spooner et al. |
| 2004/0133251 A1 | 7/2004 | Altshuler et al. |
| 2004/0143920 A1 | 7/2004 | Nanda |
| 2004/0147984 A1 | 7/2004 | Altshuler et al. |
| 2004/0156626 A1 | 8/2004 | Thoms |
| 2004/0161213 A1 | 8/2004 | Lee |
| 2004/0162549 A1 | 8/2004 | Altshuler |
| 2004/0162596 A1 | 8/2004 | Altshuler et al. |
| 2004/0176764 A1 | 9/2004 | Island et al. |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199227 A1 | 10/2004 | Altshuler et al. |
| 2004/0204745 A1 | 10/2004 | Altshuler et al. |
| 2004/0210214 A1* | 10/2004 | Knowlton .............. A61B 18/14 606/41 |
| 2004/0210276 A1 | 10/2004 | Altshuler et al. |
| 2004/0214132 A1 | 10/2004 | Altshuler |
| 2004/0225339 A1 | 11/2004 | Yaroslaysky et al. |
| 2004/0230258 A1 | 11/2004 | Altshuler et al. |
| 2004/0230260 A1 | 11/2004 | MacFarland et al. |
| 2004/0234460 A1 | 11/2004 | Tarver et al. |
| 2004/0260210 A1* | 12/2004 | Ella et al. .................. 601/7 |
| 2005/0038418 A1 | 2/2005 | Altshuler et al. |
| 2005/0049467 A1 | 3/2005 | Stamatas et al. |
| 2005/0049582 A1 | 3/2005 | DeBenedictis et al. |
| 2005/0049658 A1 | 3/2005 | Connors et al. |
| 2005/0063931 A1 | 3/2005 | Paus et al. |
| 2005/0065531 A1 | 3/2005 | Cohen |
| 2005/0085875 A1 | 4/2005 | Van Zuylen |
| 2005/0102213 A1 | 5/2005 | Savasoglu et al. |
| 2005/0107849 A1 | 5/2005 | Altshuler et al. |
| 2005/0143719 A1 | 6/2005 | Sink |
| 2005/0168158 A1 | 8/2005 | Inochkin et al. |
| 2005/0171517 A1 | 8/2005 | Altshuler et al. |
| 2005/0171581 A1 | 8/2005 | Connors et al. |
| 2005/0177026 A1 | 8/2005 | Hoeg et al. |
| 2005/0182389 A1 | 8/2005 | LaPorte et al. |
| 2005/0197681 A1 | 9/2005 | Barolet et al. |
| 2005/0215988 A1 | 9/2005 | Altshuler et al. |
| 2005/0220726 A1 | 10/2005 | Pauly et al. |
| 2005/0251118 A1 | 11/2005 | Anderson et al. |
| 2006/0004306 A1 | 1/2006 | Altshuler et al. |
| 2006/0004347 A1 | 1/2006 | Altshuler et al. |
| 2006/0009750 A1 | 1/2006 | Altshuler et al. |
| 2006/0020309 A1 | 1/2006 | Altshuler et al. |
| 2006/0047281 A1 | 3/2006 | Kreindel |
| 2006/0058712 A1 | 3/2006 | Altschuler et al. |
| 2006/0079947 A1 | 4/2006 | Tankovich et al. |
| 2006/0089687 A1 | 4/2006 | Spooner et al. |
| 2006/0094988 A1 | 5/2006 | Tosaya et al. |
| 2006/0100677 A1 | 5/2006 | Blumenkranz et al. |
| 2006/0122668 A1 | 6/2006 | Anderson et al. |
| 2006/0149343 A1 | 7/2006 | Altshulter et al. |
| 2006/0161143 A1 | 7/2006 | Altshuler et al. |
| 2006/0194164 A1 | 8/2006 | Altshuler et al. |
| 2006/0206103 A1 | 9/2006 | Altshuler et al. |
| 2006/0253176 A1 | 11/2006 | Caruso et al. |
| 2006/0265032 A1* | 11/2006 | Hennings et al. .............. 607/89 |
| 2006/0271028 A1 | 11/2006 | Altshuler et al. |
| 2006/0287646 A1 | 12/2006 | Altshuler et al. |
| 2007/0027440 A1 | 2/2007 | Altshuler et al. |
| 2007/0038206 A1 | 3/2007 | Altshuler et al. |
| 2007/0049910 A1 | 3/2007 | Altshuler et al. |
| 2007/0060819 A1 | 3/2007 | Altshuler et al. |
| 2007/0060989 A1* | 3/2007 | Deem et al. .................. 607/99 |
| 2007/0067006 A1 | 3/2007 | Altshuler et al. |
| 2007/0073308 A1 | 3/2007 | Anderson et al. |
| 2007/0073367 A1* | 3/2007 | Jones .................. A61B 18/203 607/89 |
| 2007/0078501 A1 | 4/2007 | Altshuler et al. |
| 2007/0121069 A1 | 5/2007 | Andersen et al. |
| 2007/0159592 A1 | 7/2007 | Rylander et al. |
| 2007/0185552 A1 | 8/2007 | Masotti et al. |
| 2007/0194717 A1 | 8/2007 | Belikov et al. |
| 2007/0198004 A1 | 8/2007 | Altshuler et al. |
| 2007/0213696 A1 | 9/2007 | Altshuler et al. |
| 2007/0213698 A1 | 9/2007 | Altshuler et al. |
| 2007/0213792 A1 | 9/2007 | Yaroslaysky et al. |
| 2007/0219604 A1 | 9/2007 | Yaroslaysky et al. |
| 2007/0219605 A1 | 9/2007 | Yaroslaysky et al. |
| 2007/0239142 A1 | 10/2007 | Altshuler et al. |
| 2007/0239143 A1 | 10/2007 | Altshuler et al. |
| 2007/0255355 A1 | 11/2007 | Altshuler et al. |
| 2007/0288071 A1 | 12/2007 | Rogers |
| 2008/0009842 A1 | 1/2008 | Manstein et al. |
| 2008/0058783 A1 | 3/2008 | Altshuler et al. |
| 2008/0103565 A1 | 5/2008 | Altshuler et al. |
| 2008/0132886 A1 | 6/2008 | Cohen et al. |
| 2008/0139901 A1 | 6/2008 | Altshuler et al. |
| 2008/0140164 A1 | 6/2008 | Oberreiter et al. |
| 2008/0147054 A1 | 6/2008 | Altshuler et al. |
| 2008/0154157 A1 | 6/2008 | Altshuler et al. |
| 2008/0172047 A1 | 7/2008 | Altshuler et al. |
| 2008/0183162 A1 | 7/2008 | Altshuler et al. |
| 2008/0183250 A1 | 7/2008 | Tanojo et al. |
| 2008/0186591 A1 | 8/2008 | Altshuler et al. |
| 2008/0195183 A1 | 8/2008 | Botchkareva et al. |
| 2008/0214988 A1 | 9/2008 | Altshuler et al. |
| 2008/0248554 A1* | 10/2008 | Merchant et al. ............ 435/259 |
| 2008/0294150 A1 | 11/2008 | Altshuler et al. |
| 2008/0294152 A1 | 11/2008 | Altshuler et al. |
| 2008/0306471 A1 | 12/2008 | Altshuler et al. |
| 2008/0319430 A1 | 12/2008 | Zenzie et al. |
| 2009/0048557 A1 | 2/2009 | Yeshurun et al. |
| 2009/0069741 A1 | 3/2009 | Altshuler et al. |
| 2009/0137995 A1 | 5/2009 | Altshuler et al. |
| 2009/0248004 A1 | 10/2009 | Altshuler et al. |
| 2009/0254076 A1 | 10/2009 | Altshuler et al. |
| 2009/0287195 A1 | 11/2009 | Altshuler et al. |
| 2010/0036295 A1 | 2/2010 | Altshuler et al. |
| 2010/0145321 A1 | 6/2010 | Altshuler et al. |
| 2010/0204686 A1 | 8/2010 | Yaroslavksy et al. |
| 2010/0286673 A1 | 11/2010 | Altshuler et al. |

(56) References Cited

U.S. PATENT DOCUMENTS

| | | | |
|---|---|---|---|
| 2010/0298744 | A1 | 11/2010 | Altshuler et al. |
| 2011/0046523 | A1 | 2/2011 | Altshuler et al. |
| 2011/0137230 | A1 | 6/2011 | Altshuler et al. |
| 2011/0172651 | A1 | 7/2011 | Altshuler et al. |
| 2011/0184334 | A1 | 7/2011 | Altshuler et al. |
| 2011/0267830 | A1 | 11/2011 | Altshuler et al. |

FOREIGN PATENT DOCUMENTS

| | | | |
|---|---|---|---|
| CN | 2053926 | U | 3/1990 |
| CN | 1073607 | A | 6/1993 |
| CN | 1182572 | A | 5/1998 |
| CN | 1351483 | A | 5/2002 |
| CN | 1535126 | A | 10/2004 |
| DE | 3304230 | A1 | 8/1984 |
| DE | 3719561 | A1 | 1/1988 |
| DE | 3837248 | A1 | 5/1990 |
| DE | 9102407 | U1 | 7/1991 |
| DE | 19803460 | C1 | 8/1999 |
| DE | 19944401 | A1 | 3/2001 |
| DE | 10140715 | A1 | 3/2002 |
| DE | 10112289 | A1 | 9/2002 |
| DE | 10120787 | A1 | 1/2003 |
| EP | 0000593 | A1 | 2/1979 |
| EP | 0142671 | A1 | 5/1985 |
| EP | 0172490 | A1 | 2/1986 |
| EP | 0320080 | A1 | 6/1989 |
| EP | 0324120 | A1 | 7/1989 |
| EP | 0563953 | A2 | 10/1993 |
| EP | 0565331 | A2 | 10/1993 |
| EP | 0593375 | A1 | 4/1994 |
| EP | 0598984 | | 6/1994 |
| EP | 0709941 | A1 | 5/1996 |
| EP | 0724894 | A2 | 8/1996 |
| EP | 0726083 | A2 | 8/1996 |
| EP | 0736308 | A2 | 10/1996 |
| EP | 0743029 | A2 | 11/1996 |
| EP | 0755698 | A2 | 1/1997 |
| EP | 0763371 | A2 | 3/1997 |
| EP | 0765673 | A2 | 4/1997 |
| EP | 0765674 | A2 | 4/1997 |
| EP | 0783904 | A2 | 7/1997 |
| EP | 0884066 | A2 | 12/1998 |
| EP | 0885629 | A2 | 12/1998 |
| EP | 0920840 | A2 | 6/1999 |
| EP | 0 927 544 | A2 | 7/1999 |
| EP | 1038505 | A2 | 9/2000 |
| EP | 1057454 | A2 | 12/2000 |
| EP | 1075854 | A2 | 2/2001 |
| EP | 1138349 | A2 | 10/2001 |
| EP | 1147785 | A2 | 10/2001 |
| EP | 1219258 | A1 | 7/2002 |
| EP | 1226787 | A2 | 7/2002 |
| EP | 1 238 683 | A1 | 9/2002 |
| EP | 1250893 | | 10/2002 |
| EP | 1457234 | | 9/2004 |
| EP | 1495735 | A1 | 1/2005 |
| EP | 1512373 | A1 | 3/2005 |
| EP | 1535582 | A1 | 6/2005 |
| EP | 1627662 | A1 | 2/2006 |
| EP | 1839705 | A1 | 10/2007 |
| EP | 1854505 | A2 | 11/2007 |
| FR | 2199453 | A1 | 4/1974 |
| FR | 2591902 | A1 | 6/1987 |
| GB | 1546625 | A | 5/1979 |
| GB | 2044908 | A | 10/1980 |
| GB | 2059053 | A | 4/1981 |
| GB | 2059054 | A | 4/1981 |
| GB | 2123287 | A | 2/1984 |
| GB | 2239675 | A | 7/1991 |
| GB | 2270159 | A | 3/1994 |
| GB | 2356570 | A | 5/2001 |
| GB | 2360461 | A | 9/2001 |
| GB | 2360946 | A | 10/2001 |
| GB | 2364376 | A | 1/2002 |
| GB | 2368020 | A | 4/2002 |
| GB | 2390021 | A | 12/2003 |
| GB | 2397528 | A | 7/2004 |
| JP | 54129791 | A | 10/1979 |
| JP | 64-027554 | A | 1/1989 |
| JP | 10-099574 | A | 4/1989 |
| JP | 01-181877 | A | 7/1989 |
| JP | 02-013014 | Y2 | 4/1990 |
| JP | 02-174804 | A | 7/1990 |
| JP | 03066387 | A | 3/1991 |
| JP | 06-022871 | A | 2/1994 |
| JP | 07-063957 | A | 3/1995 |
| JP | 09-084803 | A | 3/1997 |
| JP | 9141869 | A | 6/1997 |
| JP | 10-014661 | A | 1/1998 |
| JP | 10-503109 | A | 3/1998 |
| JP | 10-165410 | A | 6/1998 |
| JP | 11-047146 | | 2/1999 |
| JP | 2000-037400 | | 2/2000 |
| JP | 2000-153003 | A | 6/2000 |
| JP | 2000-300684 | | 10/2000 |
| JP | 2001-029124 | A | 2/2001 |
| JP | 2001145520 | A | 5/2001 |
| JP | 2001520534 | A | 10/2001 |
| JP | 2001-343560 | A | 12/2001 |
| JP | 2002506362 | T | 2/2002 |
| JP | 2002522110 | A | 7/2002 |
| JP | 2002272861 | A | 9/2002 |
| JP | 2005-017796 | A | 1/2005 |
| JP | 2005027702 | A | 2/2005 |
| JP | 2009106767 | A | 4/2009 |
| JP | 2009136691 | A | 6/2009 |
| RU | 2082337 | C1 | 6/1997 |
| RU | 2089126 | C1 | 9/1997 |
| RU | 2089127 | C1 | 9/1997 |
| RU | 2096051 | C1 | 11/1997 |
| RU | 2122848 | C1 | 12/1998 |
| WO | 86/002783 | | 5/1986 |
| WO | 88/004592 | | 6/1988 |
| WO | 90/000420 | | 1/1990 |
| WO | 91/02562 | | 3/1991 |
| WO | 91/013652 | | 9/1991 |
| WO | 92/016338 | | 1/1992 |
| WO | 92/019165 | | 11/1992 |
| WO | 93/005920 | | 4/1993 |
| WO | 95/10243 | | 4/1995 |
| WO | 95/015725 | | 6/1995 |
| WO | 95/032441 | | 11/1995 |
| WO | 96/22741 | | 8/1996 |
| WO | 96/023447 | | 8/1996 |
| WO | 96/24406 | A1 | 8/1996 |
| WO | 96/025979 | | 8/1996 |
| WO | 9628212 | A1 | 9/1996 |
| WO | 9636396 | | 11/1996 |
| WO | 9641579 | | 12/1996 |
| WO | 97/013458 | | 4/1997 |
| WO | 97/013552 | | 4/1997 |
| WO | 97/22384 | | 6/1997 |
| WO | 97/28752 | A1 | 8/1997 |
| WO | 98/004317 | | 2/1998 |
| WO | 98/05286 | | 2/1998 |
| WO | 98/05380 | A1 | 2/1998 |
| WO | 98/06456 | | 2/1998 |
| WO | 98/07379 | | 2/1998 |
| WO | 98/20937 | | 5/1998 |
| WO | 98/024507 | | 6/1998 |
| WO | 98/29134 | A2 | 7/1998 |
| WO | 98/41158 | | 9/1998 |
| WO | 98/051235 | | 11/1998 |
| WO | 98/052481 | | 11/1998 |
| WO | 98/058595 | | 12/1998 |
| WO | 99/10046 | | 3/1999 |
| WO | 99/17668 | A1 | 4/1999 |
| WO | 9917666 | A1 | 4/1999 |
| WO | 9917667 | | 4/1999 |
| WO | 99/027997 | | 6/1999 |
| WO | 99/029243 | | 6/1999 |
| WO | 99/34867 | | 7/1999 |
| WO | 99/038569 | | 8/1999 |

(56) References Cited

FOREIGN PATENT DOCUMENTS

| WO | 99/43387 | | 9/1999 |
|---|---|---|---|
| WO | 99/44638 | | 9/1999 |
| WO | 99/046005 | | 9/1999 |
| WO | 99/049937 | | 10/1999 |
| WO | 99/62472 | | 12/1999 |
| WO | 99/66988 | | 12/1999 |
| WO | 0002491 | | 1/2000 |
| WO | 0003257 | A1 | 1/2000 |
| WO | 00007514 | | 2/2000 |
| WO | 00/30714 | | 6/2000 |
| WO | 0032272 | A1 | 6/2000 |
| WO | 00/41278 | | 7/2000 |
| WO | 0040266 | A2 | 7/2000 |
| WO | 0043070 | A1 | 7/2000 |
| WO | 0044294 | A1 | 8/2000 |
| WO | 00/54685 | | 9/2000 |
| WO | 0054649 | A2 | 9/2000 |
| WO | 00/62700 | A1 | 10/2000 |
| WO | 00/66226 | | 11/2000 |
| WO | 0064537 | | 11/2000 |
| WO | 0071045 | A1 | 11/2000 |
| WO | 0074583 | A1 | 12/2000 |
| WO | 0074781 | A1 | 12/2000 |
| WO | 0078242 | A1 | 12/2000 |
| WO | 01003257 | A1 | 1/2001 |
| WO | 01/014012 | A1 | 3/2001 |
| WO | 01026573 | A1 | 4/2001 |
| WO | 01034048 | A1 | 5/2001 |
| WO | 01/41872 | A1 | 6/2001 |
| WO | 01042671 | A1 | 6/2001 |
| WO | 01054606 | A1 | 8/2001 |
| WO | 01054770 | A1 | 8/2001 |
| WO | 01078830 | A2 | 10/2001 |
| WO | 02/09813 | | 2/2002 |
| WO | 0226147 | | 4/2002 |
| WO | 02053050 | A1 | 7/2002 |
| WO | 02069825 | A2 | 9/2002 |
| WO | 02078559 | | 10/2002 |
| WO | 02094116 | A1 | 11/2002 |
| WO | 03/005883 | | 1/2003 |
| WO | 03049633 | | 6/2003 |
| WO | 04/000150 | | 12/2003 |
| WO | 04/011848 | | 2/2004 |
| WO | 04/033040 | | 4/2004 |
| WO | 04/037068 | A2 | 5/2004 |
| WO | 04/037287 | A2 | 5/2004 |
| WO | 04/080279 | | 9/2004 |
| WO | 04073537 | A2 | 9/2004 |
| WO | 04084752 | A2 | 10/2004 |
| WO | 04086947 | A2 | 10/2004 |
| WO | 05007003 | A1 | 1/2005 |
| WO | 05009266 | A1 | 2/2005 |
| WO | 05/030317 | | 4/2005 |
| WO | 05/46793 | | 5/2005 |
| WO | 05/065288 | | 7/2005 |
| WO | 05/92438 | | 10/2005 |
| WO | 05/096981 | | 10/2005 |
| WO | 05/099369 | | 10/2005 |
| WO | 05112815 | A1 | 12/2005 |
| WO | 06/006123 | | 1/2006 |
| WO | 06036968 | A2 | 4/2006 |
| WO | 06/066226 | | 6/2006 |
| WO | 06/089227 | | 8/2006 |
| WO | 06/101735 | A1 | 9/2006 |
| WO | 06/116141 | A1 | 11/2006 |
| WO | 07/35444 | | 3/2007 |
| WO | 07/122611 | | 11/2007 |
| WO | 08/70747 | | 6/2008 |

OTHER PUBLICATIONS

Grossman, M.C. et al., "Damage to hair follicles by normal-mode ruby laser pulses," Journal of he American Academy of Dermatology, vol. 35, No. 6, pp. 889-894, Dec. 1996.

Grossman, M.C. et al., "Laser Targeted at Hair Follicles, " Lasers Med Surg., Suppl. 7:221 (1995).
Hicks et al., "After Low Fluence Argon Laser and Flouride Treatment," Compendium, vol. 18, No. 6, Jun. 1997.
Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995.
Hsu et al., "Combined Effects of Laser Irradiation/Solution Flouride Ion on Enamel Demineralization," Journal of Clinical Laser Medicine and Surgery, vol. 16, No. 2 pp. 93-105, 1998.
Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).
Hulsbergen Henning et al., "Port Wine Stain Coagulation Experiments with a 540-nm Continuous Wave Dye-Laser," Lasers in Surgery and Medicine, 2:205-210 (1983).
Invention description to certificate of authorship, No. 719439, "The ring resonator of optical quantum generator".
Invention description to certificate of authorship, No. 741747, "The modulator of optical radiation intensity".
Invention description to certificate of authorship, No. SU 1257475 A1, "Laser interferometric device to determine no-linearity of an index of refraction of optical medium".
Invention description to certificate of authorship, No. SU 1326962 A1, "The way of determination of non-linearity of an index of refraction of optical medium".
Invention description to certificate of autorship, No. 532304, "The way of investigation of radiation time structure of optical quantum generator".
[No Author] IPG Data Sheet for TFL Thulium Laser, Jun. 2001.
Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).
Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.
Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.
Karu, "Photobiological Fundamentals of Low-Power Laser Therapy," 8th Congress of International Society for Laser Surgery and Medicine, Mar. 30, 1987.
Kazmina et al., "Laser Prophlaxis and Treatment of Primary caries," SPIE vol. 1984, pp. 231-233.
Klein, E. et al., "Biological effects of laser radiation 1.," Northeast Electroncis Research and Engineering Meeting, NEREM Record, IEEE catalogue No. F-60, pp. 108-109, 1965.
Kozlov et al., "Laser in Diagnostics and Treatment of Microcirculation Disorders Under Parodontitis," SPIE vol. 1984, pp. 253-264.
Kuhns, J.G. et al., "Biological effects of laser radiation II Effects of laser irradiation on the skin," NEREM Record, pp. 152-153, 1965.
Kuhns, J.G. et al., "Laser injury in skin," Laboratory Investigation, vol. 17, No. 1, pp. 1-13, Jul. 1967.
Levin, G. et al., "Designing with hyseretic current-mode control, " EDN Magazine, pp. 1-8, Apr. 11, 1996.
Levin, G. et al., "Designing with hyseretic current-mode control, " EDN Magazine, pp. 1-8, Apr. 28, 1994.
Maegawa, et al., "Effects of Near-Infrared Low-Level Laser Irradiation on Microcirculation," Lasers in Surgery and Medicine, vol. 27, pp. 427-437, 2000.
Mamedova et al., "Microbiological Estimate of Parodontis Laser Therapy Efficiency," SPIE vol. 1984, pp. 247-249.
Mang, "Effect of Soft Laser Treatment on Wound Healing in the Hamster Oral Mucosa," American Society for Laser Medicine and Surgery Abstracts, Chapters 25, pp. 5-8.
Manstein, D. et al., "Selective Photothermolysis of Lipid-Rich Tissue," American Society for Laser medicine and Surgery Abstracts, No. 17, American Society for Laser Medicine and Surgery Twenty-First Annual Meeting, Apr. 20-22, 2001, p. 6.

(56) References Cited

OTHER PUBLICATIONS

Margolis, R.J. et al., "Visible action spectrum for melanin-specific selective photothermolysis," Lasers in Surgery and Medicine, vol. 9, pp. 389-397, 1989.
Marinelli et al., "Diode laser illuminated automotive lamp systems," SPIE Proceedings vol. 3285:170-177 (1998).
Marshak, I.S., et al., "Pulsed Light Sources," State Power Engineering Press, Moscow and Leningrad (1963).
McDaniel, et al., "Hexascan: A New Robotized Scanning Laser Handpiece," Cutis, 45:300-305 (1990).
Nemeth, et al., "Copper vapor laser treatment of pigmented lesions," Lasers Surg. Med. Supp. 2:51 (1990).
Ohbayashi, "Stimulatory Effect of Laser Irradiation on Calcified Nodule Formation in Human Dental Pulp Fibroblasts," Abstract J-Endod. Jan. 1999; 25(1): 30-3.
Ohshiro et al., "The Ruby and Argon Lasers in the Treatment of the Naevi," Annals Academy of Medicine, Apr. 1983, vol. 12, No. 2, pp. 388-395.
Oleinik, et al., "Automatized Securing Definition for Laser Therapy Indications in Case of Non-complicated Caries," SPIE, vol. 1984, pp. 238-244.
Orchardson, "Effect of Pulsed Nd:YAG Laser Radiation on Action Potential Conduction in Nerve Fibres Inside Teeth in vitro," Abstract J-Dent. Jul.-Aug. 1998; 26(5-6): 421-6.
Osigo et al, "Phase Transitions of Rat Stratum Corneum Lipids by an Electron Paramagnetic Resonance Study and Relationship of Phase States to Drug Penetration," Biochimica et Biophysica Acta 1301:97-104 (1996).
Ozawa et al., "Stimulatory Effects of Low-Power Laser Irradiation on Bone Formation in vitro," SPIE vol. 1984, pp. 281-288.
Parrish, J.A., "Selective thermal effects with pulsed irradiation from lasers: From organ to organelle," Journal of Investigative Dermatology, vol. 80, No. 6 Supplement, pp. 75s-80s, 1983.
Petrischev et al. "Clinical and Experimental Low-Intense Laser Therapy in Dentistry," SPIE, vol. 1984, pp. 212-214.
Petrischev et al., "Report on Low Intensity Laser Radiation Usage in Dentistry," SPIE vol. 1984, pp. 202-211.
Polla, L. et al., "Melanosomes are a primary target of Q-switched ruby laser irradiation in guinea pig skin," Journal of Investigative Dermatology, vol. 89, No. 3, pp. 281-286, Sep. 1987.
Powell, "Laser Dental Decay Prevention: does it have a future?" SPIE vol. 3192, 1997.
Remillard et al., "Diode laser illuminated automotive brake lamp using a linear fanout diffractive optical element," Proc. of the Diffractive Optics and Micro-Optics Conference, OSA Technical Digest Series vol. 10, 192-194 (1998).
Remillard et al., "Diode Laser Illuminators for Night-Vision Applications," SPIE Proceedings vol. 4285:14-22 (2001).
Riggle et al., "Laser Effects on Normal and Tumor Tissue," Laser Applications in Medicine and Biology, vol. 1, M.L. Wolbarsht, editor, Plenum Press, publishers, Ch. 3, pp. 35-65 (1971).
Rohrer, "Evaluating the Safety and Efficacy of a Novel Light Based Hair Removal System," Lasers. Surg. Med. Supp. 13:97 (2001).
Rotteleur, et al., "Robotized scanning laser handpiece for the treatment of port wine stains and other angiodysplasias," Lasers Surg. Med., 8:283-287 (1998).
Rubach et al., "Histological and Clinical Evaluation of Facial Resurfacing Using a Carbon Dioxide Laser With the Computer Pattern Generator," Arch Otolaryngol Head Neck Surg., 123:929-934 (1997).
[No Author] BIOPTRON Light Therapy System. Website print-out, accessed Jul. 13, 2006 (2 pages).
[No Author] Derma Chiller advertisement (2 pages) from Paradigm Trex.
[No Author] Webpage www.gallery.com—Rutile (Titanium Oxide)—Retrieved Oct. 3, 2011 from Http://www.galleries.com/minerals/oxides/rutile/rutile.htm. 2 pages.
Altea Therapeutics—Medicines Made Better (single page website print-out).
Altshuler et al., "Human Tooth as an Optical Device," SPIE vol. 1429 Holography and Interferometry and Optical Pattern Recognition in Biomedicine, pp. 95-104, 1991.
Altshuler et al., "Modern Optics and Dentistry," Laser in Dentistry, pp. 283-297, 1995.
Altshuler et al., "New Optical Effects in the Human Hard Tooth Tissues," Lasers and Medicine, Proc. SPIE vol. 1353, pp. 97-102, 1989.
Altshuler, G.B. et al., "Acoustic response of hard dental tissues to pulsed laser action," SPIE, vol. 2080, Dental Application of Lasers, pp. 97-103, 1993.
Altshuler, G.B. et al., "Extended theory of selective photothermolysis," Lasers in Surgery and Medicine, vol. 29, pp. 416-432, 2001.
Amy, R.L. et al., "Selective mitochondrial damage by a ruby laser microbeam: An electron microscopic study," Science, vol. 15, pp. 756-758, Nov. 1965.
Anderson, R.R. et al., "Selective photothermolysis: Precise microsurgery by selective absorption of pulsed radiation," Science, vol. 220, pp. 524-527, Apr. 1983.
Anderson, R.R. et al., "The optics of human skin," Journal of Investigative Dermatology, vol. 77, No. 1, pp. 13-19, 1981.
Apfelberg et al. "Analysis of Complications of Argon Laser Treatment for Port Wine Hemangiomas with Reference to Striped Technique," Lasers in Surgery and Medicine, 2:357-371 (1983).
Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).
Belikov, A.V. et al., "Identification of enamel and dentine under tooth laser treatment," SPIE vol. 2623, Progress in Biomedical Optics Europt Series, Proceedings of Medical Applications of Lasers III, pp. 109-116, Sep. 1995.
Bjerring, P. et al., "Selective Non-Ablative Wrinkle Reduction by Laser," J Cutan Laser Ther, vol. 2, pp. 9-15, 2000.
Blankenau et al., "In Vivo Caries-Like Lesion Prevention with Argon Laser: Pilot Study," Journal of Clinical Laser Medicine and Surgery, vol. 17, No. 6, pp. 241-243, 1999.
Catalogue ILC, "High Performance flash and arc lamps," Book 3, 3rd edition.
Chan, E.K., "Effects of Compression on Soft Tissue Optical Properties," IEEE Journal of Selected Topics in Quantum Electronics, vol. 2, No. 4, pp. 943-950 (Dec. 1996).
Dabrowska, "Intravital Treatment of the Pulp with Stimulation Laser Biostimulation," Abstract Rocz-Akad-Med-Bialymst. 1997; 42(1): 168-76.
Dixon et al. "Hypertrophic Scarring in Argon Laser Treatment of Port-Wine Stains," Plastic and Reconstructive Surgery, 73:771-777 (1984).
Doukas et al., "Transdermal Drug Delivery With a Pressure Wave," Advanced Drug Delivery Reviews 56 (2004), pp. 559-579.
Dover, J.S. et al., "Pigmented guinea pig skin irradiated with Q-switched ruby laser pulses," Arch Dermatol, vol. 125, pp. 43-49, Jan. 1989.
European Search Report, European Patent Application No. 1 0012969.1, dated Jul. 13, 2011.
Finkelstein, L.H. et al., "Epilation of hair-bearing urethral grafts using the neodymium:yag surgical laser," Journal of Urology, vol. 146, pp. 840-842, Sep. 1991.
Fiskerstrand, E.J. et al., "Hair Removal with Long Pulsed Diode Lasers: A Comparison Between Two Systems with Different Pulse Structures," Lasers in Surgery and Medicine, vol. 32, pp. 399-404, 2003.
Forrest-Winchester et al., "The Effect of Infrared Laser Radiation on Dentinal Permeability in vitro," Department of Dentistry, University of Queensland Dental School, pp. 1-8, 1992.
Ginsbach et al. "New Aspects in the Management of Benign Cutameous Tumors," Laser 79 Opto-Electronics, Munich Conference Proceedings, 344-347 (1979).
Goldman, L. et al. "Treatment of basal cell epithelioma by laser radiation," JAMA, vol. 189, No. 10, pp. 773-775.

(56) References Cited

OTHER PUBLICATIONS

Goldman, L. et al., "Effect of the laser beam on the skin, III. Exposure of cytological preparations," Journal of Investigative Dermatology, vol. 42, pp. 247-251, 1964.
Goldman, L. et al., "Effect of the laser beam on the skin, Preliminary report" Journal of Investigative Dermatology, vol. 40, pp. 121-122, 1963.
Goldman, L. et al., "Impact of the laser on nevi and melanomas," Archives of Dermatology, vol. 90, pp. 71-75, Jul. 1964.
Goldman, L. et al., "Laser action at the cellular level," JAMA, vol. 198, No. 6, pp. 641-644, Nov. 1966.
Goldman, L. et al., "Laser treatment of tattoos, A preliminary survey of three year's clinical experience," JAMA, vol. 201, No. 11, pp. 841-844, Sep. 1967.
Goldman, L. et al., "Long-term laser exposure of a senile freckle," Arch Environ Health, vol. 22, pp. 401-403, Mar. 1971.
Goldman, L. et al., "Pathology, Pathology of the effect of the laser beam on the skin," Nature, vol. 197, No. 4870, pp. 912-914, Mar. 1963.
Goldman, L. et al., "Preliminary investigation of fat embolization from pulsed ruby laser impacts of bone," Nature, vol. 221, pp. 361-363, Jan. 1969.
Goldman, L. et al., "Radiation from a Q-switched ruby laser, Effet of repeated impacts of power output of 10 megawatts on a tattoo of man," Journal of Investigative Dermatology, vol. 44, pp. 69-71, 1965.
Goldman, L. et al., "Replica microscopy and scanning electron microscopy of laser impacts on the skin," Journal of Investigative Dermatology, vol. 52, No. 1, pp. 18-24, 1969.
Goldman, L. et al., "The biomedical aspects of lasers," JAMA, vol. 188, No. 3, pp. 302-306, Apr. 1964.
Goldman, L. et al., "The effect of repeated exposures to laser beams," Acta derm.-vernereol., vol. 44, pp. 264-268, 1964.
Goldman, L., "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.
Goldman, L., "Effects of new laser systems on the skin," Arch Dermatol., vol. 108, pp. 385-390, Sep. 1973.
Goldman, L., "Laser surgery for skin cancer," New York State Journal of Medicine, pp. 1897-1900, Oct. 1977.
Goldman, L., "Surgery by laser for malignant melanoma," J. Dermatol. Surg. Oncol., vol. 5, No. 2, pp. 141-144, Feb. 1979.
Goldman, L., "The skin," Arch Environ Health, vol. 18, pp. 434-436, Mar. 1969.
Goldman, L., Biomedical Aspects of the Laser, Springer-Verlag New York Inc., publishers, Chapts. 1, 2 & 23, 1967.
Gottlieb, I., "Power Supplies, Switching Regulators, Inverters & Converters," 1976.
Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).
Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.
Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).
Sandford et al., "Thermal Effects During Desensitisation of Teeth with Gallium-Aluminum-Arsenide Lasers," University of Queensland Dental School, Periodontology 15: 25-30 (1994).
Schindl, "Does Low Intensity Laser Irradiation Really Cause Cell Damage?" Laser in Surgery and Medicine vol. 22, pp. 105, 2001.
Sheehan-Dare, et al., "Lasers in Dermatology," British Journal of Dermatology, 129:1-8 (1993).
Shimbashi, T. et al., "Ruby laser treatment of pigmented skin lesions," Aesth. Plast. Surg., vol. 19, pp. 225-229, 1995.

Shimizu et al., "Prospect of Relieving Pain Due to Tooth Movement During Orthodontic Treatment Utilizing a Ga—Al As Diode Laser," SPIE vol. 1984, pp. 275-280.
Shumilovitch et al., "Influence of Low Intensity Laser Radiation Upon the Microflora of Carious Cavities and Root Canal," SPIE vol. 1984, pp. 215-220.
Sing, "Electroacupuncture and Laser Stimulation Treatment: Evaluation by Somatosensory Evoked Potential in Conscious Rabbits," Abstract AM-J-Chin-Med. 1997; 25(3-4): 263-71.
Sliney et al., "Safety with Lasers and Other Optical Sources: A Comprehensive Handbook," Plenum Press, pp. 477-480 (1980).
Sokolova et al., "Low-intense Laser Radiation in Complex Treatment of Inflammatory Diseases of Parodontium," SPIE vol. 1984, pp. 234-237.
Stratton, K. et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.
Sumian, C.C. et al., "A Preliminary Clinical and Histopathological Study of Laser Skin Resurfacing Using a frequency-Doubled Nd:YAG Laser After Application of Chromofilma®," Journal of Cutaneous Laser Therapy, vol. 1, pp. 159-166, 1999.
Sumian, C.C. et al., "Laser Skin Resurfacing Using a Frequency Doubled Nd:YAG Laser After Topical Application of an Exogenous Chromophore," Lasers in Surgery and Medicine, vol. 25, pp. 43-50, 1999.
Taylor, C.R. et al., "Treatment of tattoos by Q-switched ruby laser," Arch. Dermatol. vol. 126, pp. 893-899, Jul. 1990.
Togatov, V.V. et al., "Discharge Circuit for Solid-State Lasers Pumping," Optical Journal, V. 67, n. 4, pp. 92-96 (2000).
Tuchin, V.V., "Laser light scattering in biomedical diagnostics and therapy," Journal of Laser Applications, vol. 5, No. 2-3, pp. 43-60, 1993.
Unger, W.P., Laser hair transplantation III: Computer-assisted laser transplanting. Dermatol Surg. 1995;21:1047-1055.
Van Bruegel, "Power Density and Exposure Time of He—Ne Irradiation Are More Important Than Total Energy Dose in Photo-Biomodulation of Human Fibroblasts in Vitro," Lasers in Surgery and Medicine, vol. 12 pp. 528-537, 1992.
Walsh, "Laser "Curettage": a Critical Analysis," Periodontology 14:4-12, 1993.
Walsh, "The Current Status of Low Level Laser Therapy in Dentistry. Part 1. Soft Tissue Applications" paper prepared by LJ Walsh, Department of Dentistry University of Queensland, pp. 1-16. Publication date unknown.
Watanabe, S. et al., "Comparative studies of femtosecond to microsecond laser pulses on selective pigmented cell injury in skin," Photochemistry and Photobiology, vol. 53, No. 6, pp. 757-762, 1991.
Watanabe, S. et al., "The Effect of Pulse Duration on Selective Pigmented Cell Injury by Dye Lasers," The Journal of Investigative Dermatology, 88:523, 1987.
Welch, A.J. et al., "Evaluation of cooling techniques for the protection of the epidermis during HD-yag laser iradiation of the skin," Neodymium-Yag Laser in Medicine and Surgery, Elsevier Science Publishing Co., publisher, pp. 195-204, 1983.
Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.
Yules, R.B. et al., "The effect of Q-switched ruby laser radiation on dermal tattoo pigment in man," Arch Surg, vol. 95, pp. 179-180, Aug. 1967.
Zeitler, E. et al., "Laser Characteristics that Might be Useful in Biology," Laser Applications in Medicine and Biology, vol. I, M.L. Wolbarsht, editor, Plenum Press, publishers, Chapter 1, pp. 1-18, 1971.
Zonios et al., "Skin Melanin, Hemoglobin, and Light Scattering Properties can be Quantitatively Assessed in Vivo Using Diffuse Reflectance Spectroscopy," Journal of Investigative Dermatology,117:1452-1457 (Dec. 2001).

(56) References Cited

OTHER PUBLICATIONS

European Office Action dated Dec. 5, 2011 for Application No. 10012155.7 (3 Pages).
European Search Report dated Mar. 1, 2011 for Application No. 10012971.7.
European Search Report dated Mar. 1, 2011 for Application No. 10012972.5.
International Preliminary Report on Patentability dated Oct. 8, 2007 for Applciation No. PCT/US2006/035927.
International Preliminary Report on Patentability dated Dec. 7, 2007 for Application No. PCT/US2007/086827.
International Search Report dated Dec. 28, 2007 for Application No. PCT/US2007/089090.
International Search Report dated May 8, 2008 for Application No. PCT/US2007/089090.
International Preliminary Report on Patentability dated Oct. 13, 2011 for Application No. PCT/US2010/030010.

* cited by examiner

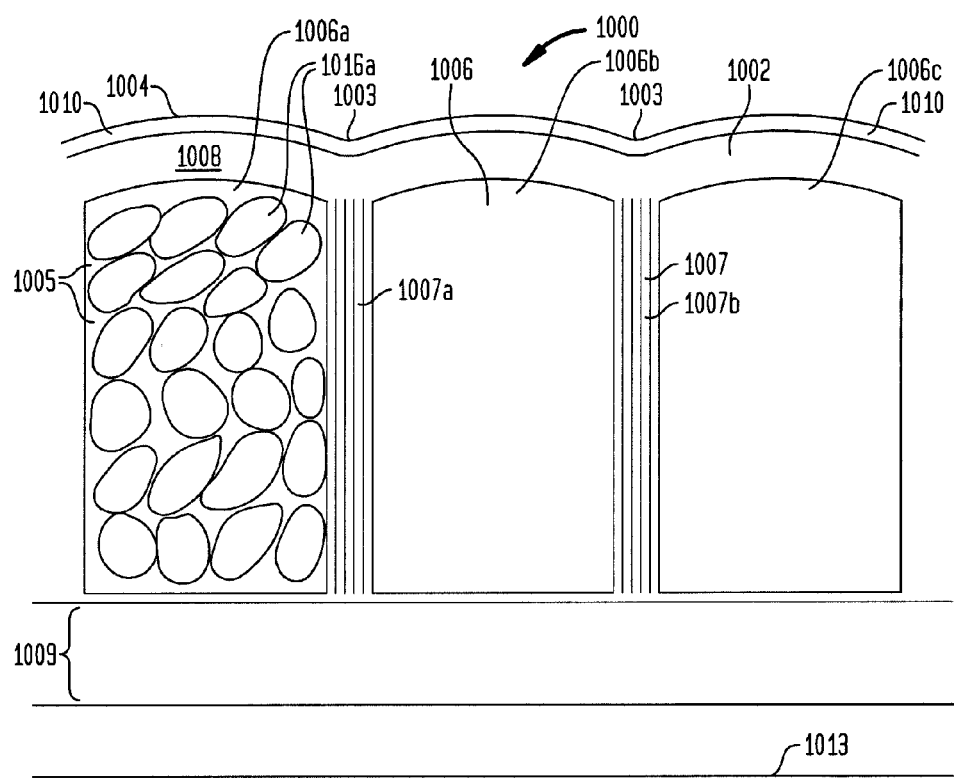

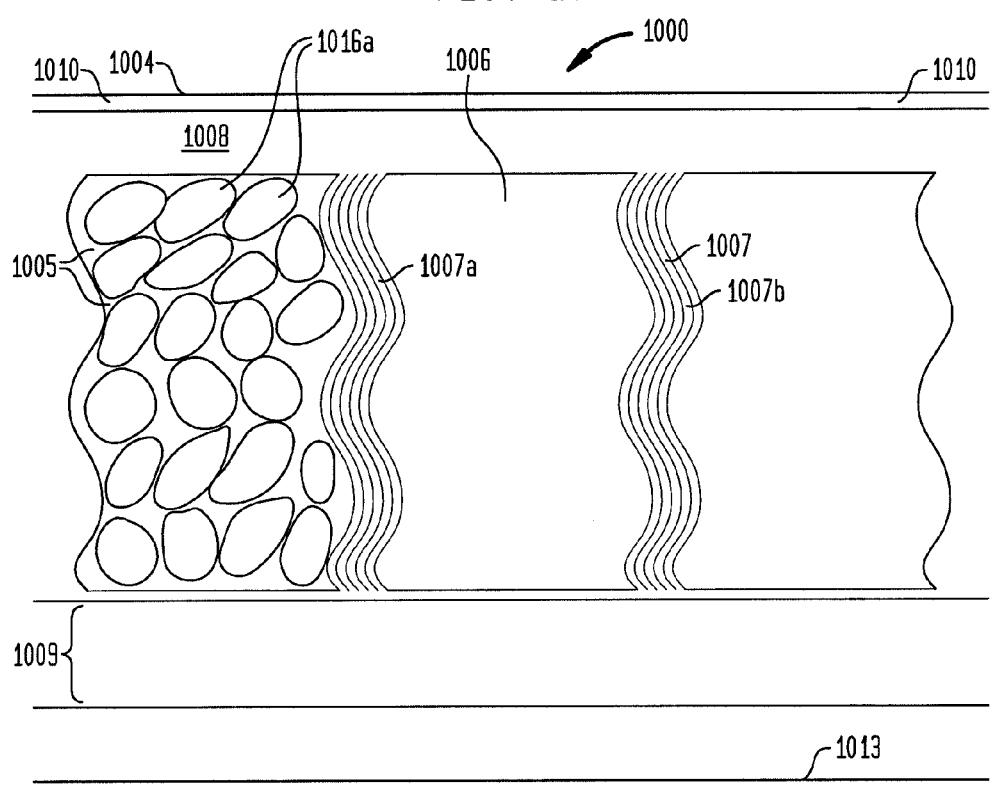

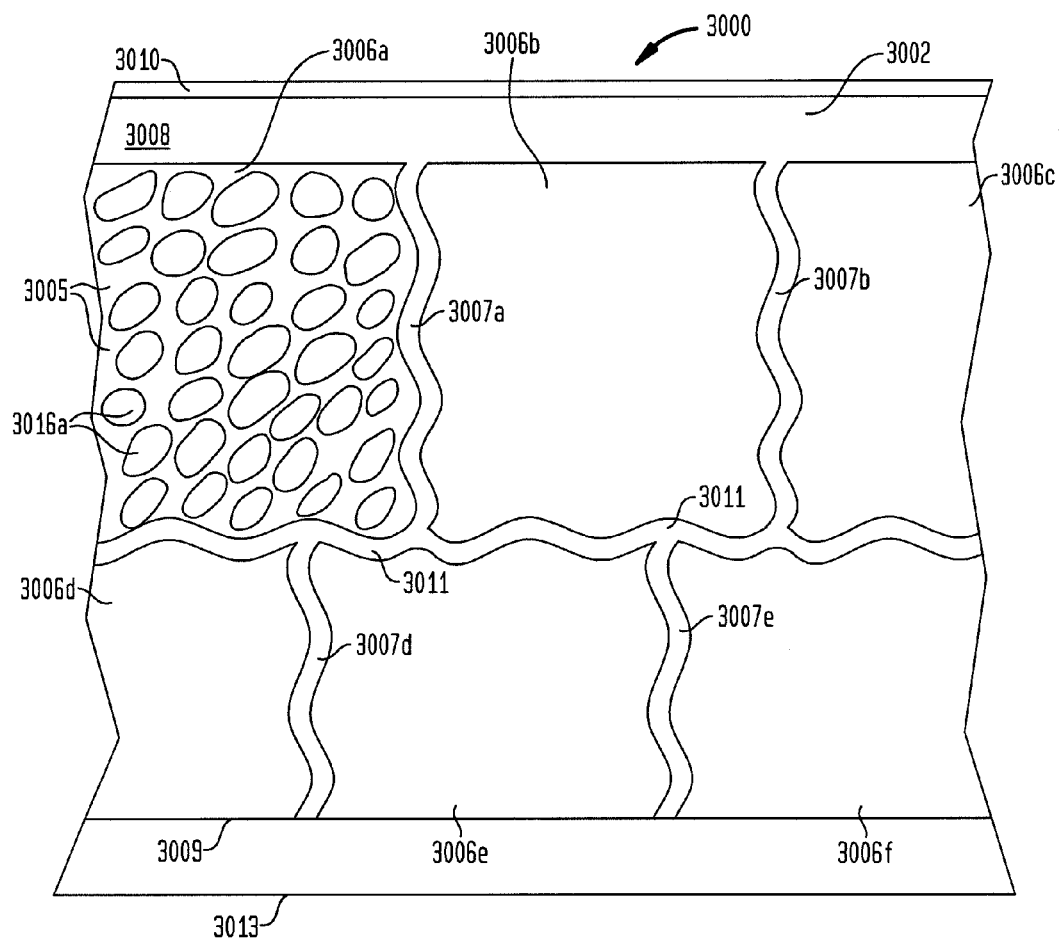

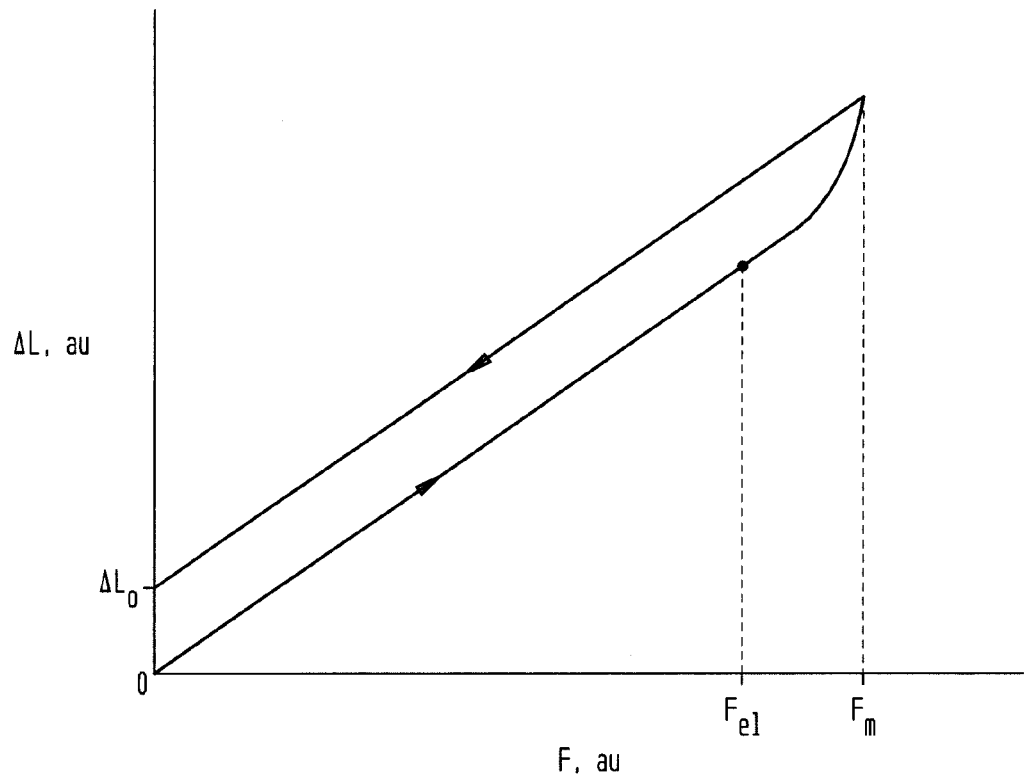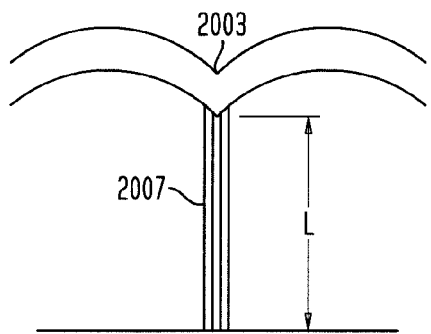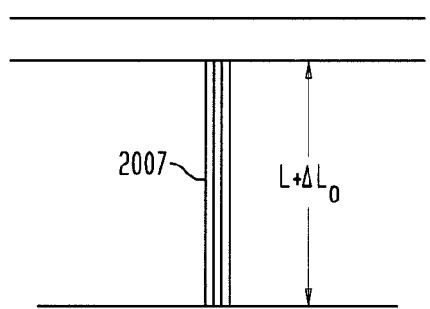

METHOD FOR IMPROVEMENT OF CELLULITE APPEARANCE

RELATED APPLICATION

The present application claims priority to a provisional application entitled "Method for Improvement of Cellulite Appearance" and having U.S. Ser. No. 61/271,593. This provisional application is herein incorporated by reference in its entirety.

BACKGROUND OF THE INVENTION

The appearance of cellulite on a person's body can create a perception that the person is unfit and/or overweight. Individuals, generally women who have cellulite, often view it as unflattering and as a source of embarrassment. It is desirable to improve and/or eliminate the appearance of cellulite such that the appearance of cellulite is improved and/or eliminated in one or more locations of a subject's body for a relatively long period of time. It is most desirable to achieve a long term and/or durable improvement and/or to eliminate the appearance of cellulite in treated regions.

SUMMARY OF THE INVENTION

In accordance with the methods and devices disclosed herein the invention relates to the treatment of connective tissue in a subject's body to improve the appearance of cellulite on a subject's body. In some embodiments, the methods and devices treat connective tissue with substantially lasting, durable and/or irreversible results. Long lasting, durable and/or irreversible treatment of connective tissue can improve the appearance of cellulite for a relatively long period of time and/or substantially permanently.

In one aspect, the invention relates to a method of improving the appearance of cellulite and the method includes applying a stretching force to at least one of a septa tissue and a fascia tissue that is adjacent to fat tissue and is located beneath a region of a subject's skin having the appearance of cellulite. At least one of the septa tissue and the fascia tissue are heated for a period of time and at a temperature less than is required to fully coagulate any of the septa tissue, the fascia tissue and the fat tissue. In some embodiments, there is heating with no coagulation. After heating the length of at least one of the septa tissue and the fascia tissue is increased relative to the length of at least one of the septa tissue and the fascia tissue prior to applying the stretching force and/or the heating. The method can also include the step of removal of the stretching force. Improvement of the appearance of cellulite can be determined by visual inspection of the region of the subject's skin that is treated.

In another aspect, the invention relates to a method of improving the appearance of cellulite. The method includes applying a stretching force to at least one of a septa tissue and a fascia tissue that is adjacent to fat tissue and is beneath a region of a subject's skin having the appearance of cellulite. The method also includes heating at least one of the septa tissue and the fascia tissue for a period of time and at a temperature sufficient to achieve lasting elongation of at least one of the septa tissue and the fascia tissue upon release of the stretching force. In some embodiments, applying the stretching force and heating at least one of the septa tissue and the fascia tissue occur simultaneously. In other embodiments, heating of at least one of the septa tissue and the fascia tissue occurs in the presence of the previously applied stretching force.

In one embodiment, vacuum pressure applies the stretching force. Applying the stretching force can include inserting fluid into the subject's tissue. The fluid can be, for example, tumescent fluid or gas. Optionally, the fluid can be preheated such that the fluid itself provides heat at least one of the septa tissue and the fascia tissue. In another embodiment, one or more of radiofrequency energy, ultrasound energy, light energy, and microwave energy are employed to heat at least one of the septa tissue and the fascia tissue.

The method of improving the appearance of cellulite can further include employing a cannula to apply an energy source to heat at least one of the septa tissue and the fascia tissue. A suitable cannula can apply one or more of radiofrequency energy, ultrasound energy, light energy, and microwave energy to at least one of the septa tissue and the fascia tissue.

In one embodiment, heating includes bringing the temperature of at least one of the septa and the fascia to the temperature range from about 37° C. to about 60° C., or from about 40° C. to about 48° C. In accordance with methods of improving the appearance of cellulite, the increase in temperature of at least one of the septa and the fascia can also heat the surrounding subcutaneous tissue (e.g., fat tissue) in the region of the targeted fascia and/or septa tissue.

In one embodiment, at least one of the septa tissue and the fascia tissue are heated for a period of time that ranges from about 10 seconds to about 60 minutes or from about 30 seconds to about 30 minutes. The method can also include cooling the external surface of the region of the subject's skin. The method can also include the step of removal of the stretching force.

Improvement of the appearance of cellulite can be determined by visual inspection of the region of the subject's skin that has been treated.

DESCRIPTION OF THE DRAWINGS

FIG. 1B is a schematic view of the inside of a female subject's body of FIG. 1A where the region of tissue is stretched (by an external device or by the addition of tumescent fluid, which is injected inside the female subject's body) to increase the volume of the subcutaneous tissue region thereby enabling connective tissue (e.g., septa) in the subcutaneous tissue region to be stretched in a manner that is substantially lasting, durable and/or irreversible.

FIG. 1C is a schematic view of the inside of a female subject's body of FIG. 1B after the stretching force is removed (e.g., the external device is removed or the tumescent fluid is removed) and the connective tissue (e.g., septa) remains stretched in a manner that is substantially lasting, durable and/or irreversible.

FIG. 2C is a schematic view of the inside of a female subject's body of FIG. 2B after the stretching force is removed (e.g., the external device is removed or the tumescent fluid is removed) and the connective tissue (e.g., septa and fascia) remains stretched in a manner that is substantially lasting, durable and/or irreversible.

FIG. 3A shows a diagram of the generalized relationship of force applied to connective tissue on the x axis and the elongation of the connective tissue in response to the applied force on the y axis.

FIG. 3B shows a cellulite dimple under which fascia having a length L is located prior to elongation treatment.

FIG. 3C shows the improvement in the appearance of the cellulite dimple previously shown in FIG. 3B due to the elongation treatment of the fascia, after elongation treatment the fascia has a length of L+ΔLo.

DETAILED DESCRIPTION

Anatomically, the cutaneous formation of cellulite is often due to fibrosis of the connective tissues present in the dermis and/or in the subcutaneous tissue. Connective tissue of the reticular dermis is connected to the deep fascia by fibrous septum from adipose or fat tissue. Subcutaneous fat lobules are separated from each other by fibrous septum (i.e., septa), which are generally relatively thin and usually rigid strands of connective tissue. The fibrous septa cross the fatty layer and connect the dermis to the underlying fascia tissue. The septa stabilize the subcutis and divide the fat tissue. Shortening of these septa due, for example, to fibrosis, causes retraction of the septa which in turn causes the depressions in the skin that are recognized as cellulite.

Thus, cellulite appears in the subcutaneous level of skin tissue where fat cells are arranged in chambers of fat tissue that are surrounded by bands of connective tissue called septae and/or fascia. Under certain conditions, for example, as water is retained, fat cells held within the perimeters of these fat tissue chambers expand and stretch the connective tissue. In some situations, the septa tissue is physiologically short and/or the septa tissue contracts and hardens holding the skin at a non-flexible length, while the surrounding tissue continues to expand with weight, or water gain, which results in areas of the skin being held down while other sections bulge outward, resulting in the lumpy, "cottage-cheese" appearance recognized as cellulite.

Figure 1A:
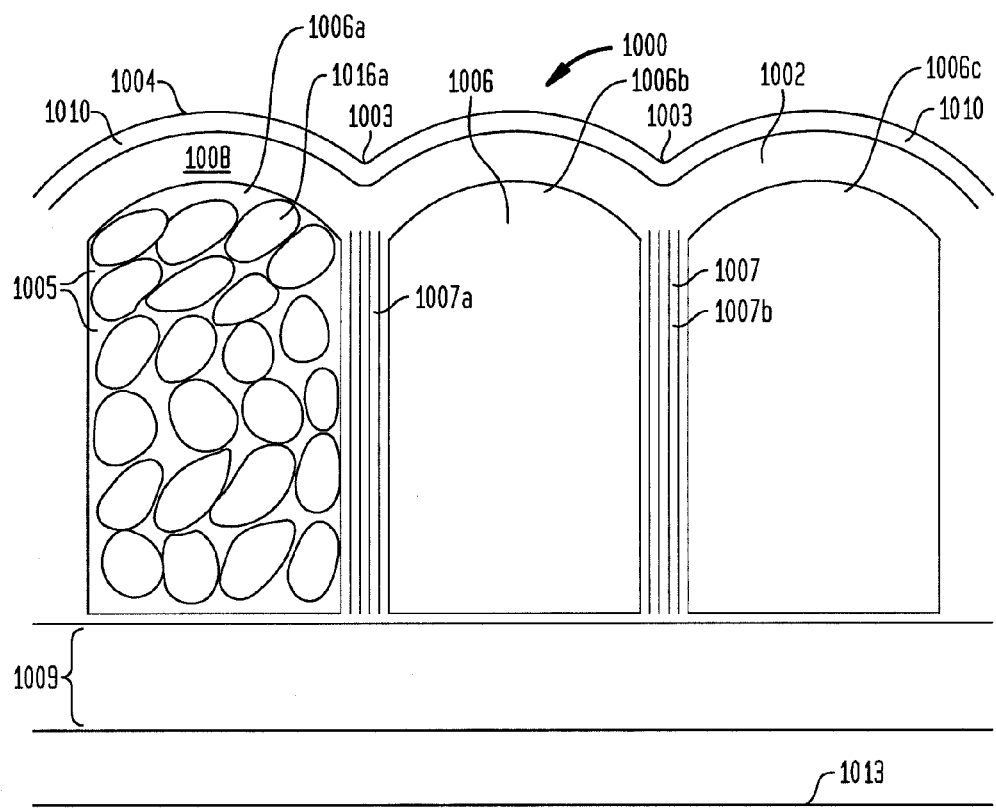
FIG. 1A is a schematic view of the inside of a female subject's body in a region of cellulite; the schematic view depicts the subcutaneous tissue, which is located between the skin (e.g., the epidermis and dermis) and muscle and bone. The subcutaneous tissue includes a relatively thin layer (e.g., a single layer) of subcutaneous fat.

Referring now to FIG. 1A, inside a female subject's body 1000, between muscle 1009 and dermis 1008 is connective tissue called fiber stents or septa 1007. In some embodiments, bone 1013 is adjacent to muscle 1009. Fiber septa 1007 are bundles of connective tissue fibers that are held between the dermis 1008 and the muscle 1009. As discussed here, fiber stents include soft tissue such as fibrous septa, which is composed of collagen fiber material similar to what is found in the dermis tissue, vascular tissue, and lymph tissue. Septa 1007 align and connect the muscle 1009 and the dermis 1008 to one another. The septa 1007 traverse through at least a portion of fat tissue 1006 inside the subject's body 1002. In some subject's, generally in females, when a volume of fat tissue 1006 between septa 1007 (e.g., between one septae 1007a and another septae 1007b) is over a threshold amount it creates an uneven, dimpled, and/or bumpy appearance on the external portion of the body 1004 and these dimples 1003 and/or bumps in the tissue are recognized as cellulite appearance. Cellulite appears due to the interaction of the existing fat 1006 with the septa 1007. A person with low fat could have cellulite because they have tight septa 1007. In some instances, cutting the septa 1007 in the region of the dimples 1003 e.g., in the areas between the bumps with a knife to relieve the stress caused by the volume of fat tissue 1006 between septa 1007 (e.g., adjacent septa 1007a and 1007b) provides relief to the stress on the skin tissue that previously resulted in a dimpled and/or bumpy appearance. Cutting the septa 1007 can result in a flattening of the skin that was formerly bumpy in the region of the septa 1007. However, cutting the septa 1007 inside the skin is dangerous because it risks unintended consequences including nerve damage and muscle damage, for example.

Cellulite is generally a problem for females but is less common in males. In females the septa 1007 between the dermis 1008 and the muscle 1009 are substantially vertical relative to the plane of the dermis 1008 and/or the plane of the muscle 1009. Generally, the fibrous septa in women are orientated in a direction perpendicular to the cutaneous surface. In contrast, males have septa between the dermis and the muscle that are shifted to the side at an angle relative to the substantially vertical direction of the septa found in females. In males the septa have an angled or criss-cross pattern that does not feature the perpendicular direction relative to the cutaneous surface. Without being bound to a single theory, it is believed that the shifted angle of septa found in males provides a level of "give" that enables changes in fat quantity inside a male's body to not result in the cellulite appearance. In addition, subcutaneous fat is divided into lobules and in women the fat lobules are relatively larger and more rectangular when compared with the fat lobules found in men. The substantially vertical septa 1007 found in females does not afford the "give" provided by the criss-cross pattern in males, further, the relatively larger size of fat lobules in women contribute to the cellulite appearance problem being more common for females than for males.

Thus, the substantially vertically oriented septa 1007 in females are primarily responsible for the typical orange peel/bumpy appearance that is recognized as cellulite. FIG. 1A depicts body areas having relatively thin subcutaneous fat (e.g., a single layer of fat tissue 1006) such as, for example, the under arms and the abdomen (i.e., the belly). The relative thickness or thinness of a body area will vary depending on individual anatomy.

Figure 2A:
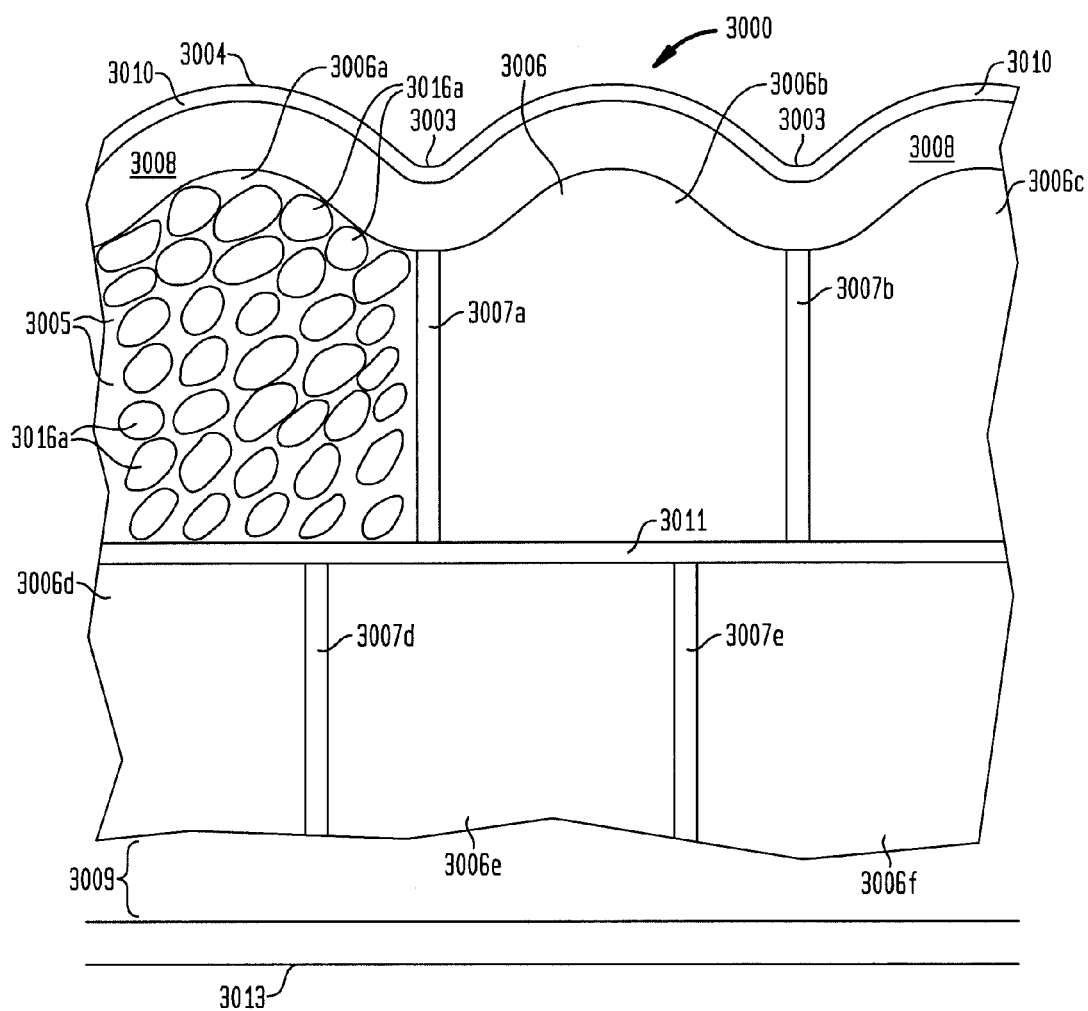
FIG. 2A is a schematic view of the inside of a female subject's body in a region of cellulite; the schematic view depicts the subcutaneous tissue, which is located between the skin (e.g., the epidermis and dermis) and muscle and bone. The subcutaneous tissue includes a relatively thick layer (e.g., a multiple layers) of subcutaneous fat.

FIG. 2A like FIG. 1A shows a female subject's body 3000, more specifically, shows the inside 3002 of a female subject's body. FIG. 2A depicts a body area having a relatively thick layer of subcutaneous fat made up of multiple chambers of fat tissue (e.g., 3006a, 3006b, 3006c, 3006d, 3006e, and 3006f) some of which are stacked on one another (e.g., 3006b and 3006e). Relatively thick layers of subcutaneous fat that are made up of multiple chambers of fat tissue can include, for example, the buttocks and/or the thighs. The inside of a female subject's body 3000 under the epidermis 3010, between muscle 3009 and dermis 3008 includes connective tissues including septa 3007 (also referred to as fiber stents) and fascia 3011. In some embodiments body areas that include cellulite have bone 3013 adjacent to muscle 3009.

A woman's anatomy features connective tissue including one or more substantially vertical septa 3007; the substantially vertical septa 3007 are substantially vertical relative to at least one of the fascia 3011, the muscle 3009, and/or the skin (e.g., the epidermis 3010 and the dermis 3008). The septa 3007 traverse through at least a portion of fat tissue 3006 inside the subject's body 3002. Referring still to FIG. 2A in body areas having a relatively thick layer of subcutaneous fat, multiple layers of fat tissue 3006 are stacked between, above and below connective tissue. More specifically, inside the subject's body 3002 in the region of some body areas having a relatively thick region of subcutaneous fat, the fat tissue 3006 is stacked between substantially vertical septa 3007 and above and below substantially horizontal fascia 3011. In some embodiments, the fat tissue 3006 chambers (e.g., 3006a, 3006b, 3006c, 3006d, 3006e, and 3006f) have an irregular pattern.

The connective tissue including the septa 3007 and the fascia 3011 align and connect the muscle 3009 and the dermis 3008 to one another. In some subjects, generally in females, when a volume of fat tissue 3006 between connective tissue 3007 (e.g., between one septa 3007b another septa (e.g., 3007a and 3007d) and fascia 3011) is over a threshold amount it creates an uneven, dimpled, and/or bumpy appearance on the external portion of the body 3004 and these dimples 3003 and/or bumps in the tissue are recognized as cellulite appearance. Cellulite appears due to the interaction of the existing fat 3006 with the connective tissue (e.g., the septa 3007 and/or the fascia 3011). Without being bound to any single theory it is believed that in some embodiments, the fascia 3011 connects to the septa 3007 and acts as an anchor that holds the septa 3007 in a position that increases the pull of the septa 3007 against the dermis 3008 and/or the epidermis 3010 and this tension/pull contributes to the cellulite appearance provided by the dimples 3003.

FIG. 3A is a diagram that shows the generalized relationship of force applied to connective tissue and the elongation of the connective tissue in response to the applied force. The force applied to connective tissue (e.g., septa and/or fascia) is shown on the x axis (force shown as F in arbitrary units (au)) and the y axis shows the elongation of the connective tissue (e.g., septa and/or fascia) as ΔL (in arbitrary units). The x axis also shows $F_{el}$ which is the elasticity limit of the connective tissue being treated. The elasticity limit is the maximum force which provides a change in length ΔL of the connective tissue that is directly proportional to the applied force F. The x axis also shows $F_m$, which is the maximum force applied during a given elongation treatment. The y axis shows ΔLo, which is the lasting elongation after releasing the force F applied to the connective tissue. Lasting elongation includes elongation that lasts for several hours after treatment, e.g., two or more hours after treatment and can include elongation that is substantially irreversible (i.e., elongation that is maintained and is substantially permanent) after treatment.

FIG. 3B shows a cellulite dimple 2003 under which septa 2007 having a length L is located prior to treatment. FIG. 3C shows the improvement in the appearance of the cellulite dimple previously shown in FIG. 3B due to the elongation treatment of the septa 2007. After the elongation treatment the septa 2007 in FIG. 3B has a length of (L+ΔLo).

As seen in FIG. 3A when the maximum force $F_m$ is higher than the elasticity limit $F_{el}$ then elongation of the connective tissue becomes non-linear such that it responds to the applied force that is greater than $F_{el}$ in a non-linear manner. After releasing the applied force F the length of the connective tissue demonstrates hysteresis behavior as is shown in FIG. 3A, which results in the lasting elongation having the quantity depicted as ΔLo. The $F_{el}$ can be a function of the tissue temperature and the time of application of the temperature to tissue. By elevating tissue temperature, the $F_{el}$ may be lowered and the lasting elongation ΔLo can be achieved with the relatively lower Force than is required in the absence of an elevated temperature. Thus, by increasing the temperature of the connective tissue to be treated with a force F the amount of force required to improve the length of (e.g., elongate) the connective tissue is reduced. In this way, negative side effects to the body area being treated including tearing, bruising and pain can be reduced and/or avoided.

Without being bound to any single theory it is believed that similar improvement of the appearance of cellulite may be achieved by exposing at least one of the fascia and/or the septa to a relatively cold temperature (e.g., from about −5° C. to about 20° C., or from about 0° C. to about 10° C.) and a stretching force (applied simultaneous with or subsequent to exposure of the tissue to the cold temperature). This stretching force may be applied to the tissue for a time period that ranges from about 1 second to about 1 hour in order to achieve a lasting elongation of the septa and/or the fascia in order to a fracture the septa and/or the fascia, both elongation and fraction are believed to improve cellulite appearance. Cooling can be done externally by employing a cold plate with circulated water, a thermoelectric cooler, an ice pack or any other suitable external cooling means. Cooling may also be done internally by, for example, injecting cooled fluid into the treatment area (e.g., cooled tumescence or cooled water) or by inserting a cooled cannula to the treatment area.

In accordance with any method(s) or device(s) for elongating connective tissue disclosed herein, a chemical such as glycerol may be added to the connective tissue prior or during the elongation process. The chemical such as glycerol can enhance elasticity of the connective tissue to increase the amount of elongation achieved in accordance with the methods and devices disclosed herein.

Treatment of Subcutaneous Tissue by Stretching Connective Tissue

In one embodiment, referring now to FIG. 1A, the substantially vertical septa 1007 (also referred to as stents) that lie between the muscle 1009 and the dermis 1008 can be stretched in order to elongate the septa 1007 and to provide "give" to the septa 1007 that avoids and/or lessens the appearance of cellulite caused by substantially vertical septa 1007 in females. In some embodiments, the septa 1007 is stretched in a manner that is substantially lasting, durable and/or irreversible. In some embodiments, a septa 1007 is determined to be stretched in a lasting or durable manner such that the septa retains its elongated length for a period that ranges from about 1 hour to about 20 years, from about 2 hours to about 5 years, or from about thirty minutes to about 1 year.

In one embodiment, the septa 1007 (i.e., the stents) are heated to a temperature in the range of from about 37° C. to about 100° C., or from about 38° C. to about 60° C., from about 44° C. to about 60° C., or from about 45° C. to about 50° C. In some embodiments, the temperature range is selected to avoid full coagulation of tissue in the region of the septa 1007. Stretching can be applied to the substantially vertical septa 1007 to increase the length of each septum by a percentage increase that ranges from about 2% to about 70%, or from about 5% to about 50% from the length of the septum prior to stretching. Stretching can be applied simultaneously or after heating within a prescribed temperature range.

In one embodiment, the septa 1007 are heated to a temperature in the range of from about 37° C. to about 100° C., or from about 38° C. to about 60° C., from about 44° C. to about 60° C., or from about 45° C. to about 50° C. and simultaneously and/or subsequent to heating a stretching action is applied to the septa for a period of time necessary to maintain a substantially lasting, durable and/or irreversible extension of the septa 1007. The period of time over which the stretching action can be applied can range from about a tenth of a second to about 24 hours, from about a tenth of a second to about 1 second, from about 30 seconds to about 24 hours, or from about 1 minute to about 1 hour or from about 10 minutes to about 30 minutes.

Over time in a subject's life time the elasticity of their connective tissue (including septa and fascia) can decline for example due to contraction and hardening of connective tissue. The decline in connective tissue can be due, for example, to sclerosis which makes the connective tissue become less flexible or elastic. This loss of elasticity contributes to the cellulite appearance. In other embodiments, referring to FIG. 2A the septa 3007 and/or the fascia 3011 that lie between the muscle 3009 and the dermis 3008 can be stretched in order to elongate the septa 3007 and/or stretch the fascia 3011 to provide "give" to the septa 3007 and/or the fascia 3011 to improve the loss of elasticity associated with cellulite. Stretching the septa 3007 and/or the fascia 3011 can avoid and/or lessen the appearance of cellulite caused by substantially vertical septa 3007 and/or fascia 3011 that has lost elasticity in females.

The septa 3007 and/or the fascia 3011 may be stretched in a manner that is substantially lasting, durable and/or irreversible. In some embodiments, septa 3007 and/or fascia 3011 is determined to be stretched in a lasting or durable manner when the connective tissue (e.g., the septa 3007 and/or the fascia 3011) retains its elongated length for a period that ranges from about 1 hour to about 20 years, from about 2 hours to about 5 years, or from about thirty minutes to about 1 year. The connective tissue (e.g., the septa 3007 and/or the fascia 3011) may be heated to a temperature in the range of from about 37° C. to about 100° C., or from about 38° C. to about 60° C., from about 44° C. to about 60° C., or from about 45° C. to about 50° C. Temperature ranges may be selected to avoid melting and/or to avoid full coagulation of tissue in the region of the septa 3007 and/or the fascia 3011. Stretching can be applied to the connective tissue (i.e., the substantially vertical septa 3007 and the connective tissue 3011) to increase the length of each septum by a percentage increase that ranges from about 2% to about 70%, or from about 5% to about 50% from the length of the connective tissue prior to stretching. Stretching can be applied simultaneously or after heating within a prescribed temperature range.

In one embodiment, the connective tissue (e.g., septa 3007 and/or fascia 3011) are heated to a temperature in the range of from about 37° C. to about 100° C., or from about 38° C. to about 60° C., from about 44° C. to about 60° C., or from about 45° C. to about 50° C. and simultaneously and/or subsequent to heating a stretching action is applied to the septa for a period of time necessary to maintain a substantially lasting, durable and/or irreversible extension of the septa. The period of time over which the stretching action can be applied can range from about a tenth of a second to about 24 hours, from about a tenth of a second to about 1 second, from about 30 seconds to about 24 hours, or from about 1 minute to about 1 hour or from about 10 minutes to about 30 minutes.

The temperature rise in septa and/or the fascia can be implemented in an internal manner and/or an external manner.

Internal Temperature Change Implementation

An internal temperature rise in septa and/or fascia can be implemented internally via an incision in the tissue of a subject and by delivering a probe into the subject's tissue through the incision. The probe can include a tip, for example a tip of a handpiece that emits energy. The tip can be inserted into a subject's tissue in the region of connective tissue to be treated, e.g., septa 1007 and fascia. The clinical endpoint of such treatment is when the connective tissue to be treated (e.g., the septa and/or the fascia) has reached a temperature of from about 45° C. to about 60° C., or from about 44° C. to about 50° C. or more generally a temperature that is less than the temperature at which the connective tissue being treated becomes fully coagulated.

The handpiece tip can emit, for example, a laser or other light emission, ultrasound energy, ohmic resistance that generates energy by simple current, microwave energy, and/or radio frequency energy (e.g., RF energy). These energy sources can have a power level of from about 1 watt to about 100 watts, or from about 10 watts to about 60 watts. The size of the tip can be from about 1 mm to about 6 mm, or from about 1 mm to about 2 mm. Where the energy source is a laser the wavelength can range from about 600 nm to 2300 nm or from about 900 nm to about 1850 nm.

In another embodiment, the handpiece tip can be heated by circulating a fluid such as, for example, hot water inside the tip. The tip temperature can range from about 50° C. to about 100° C.

In another embodiment, a preheated fluid (i.e., a preheated tumescent fluid) or a preheated gas can be injected into an internal region of a subject's body to preheat a volume of the tissue. The preheated fluid is heated up to about 60° C. or from about 40° C. to about 60° C. The temperature of the connective tissue being treated by internal treatment or external treatment can be measured by any of a number of means including, for example, inserting a thermal measurement probe that measures the connective tissue being treated. Thermal probes can be employed to measure and/or enable control of the temperature rise in the connective tissue (e.g., septa and/or fascia) being treated via feedback control such that desired clinical endpoint of connective tissue treatment is when the connective tissue to be treated (e.g., the septa and/or the fascia) has reached a temperature below the temperature of full coagulation for example, from about 37° C. to about 100° C., or from about 38° C. to about 60° C., from about 44° C. to about 60° C., or from about 45° C. to about 50° C. Thus in some embodiments the temperature change of the connective tissue form normal body temperature 37° C. ranges from about 7° C. to about 23° C. In one embodiment, internal heating heats a selected volume and/or region of a subcutaneous tissue. In another embodiment, internal heating selectively heats the fascia and/or the septa 1007 themselves. In another embodiment, internal heating heats a portion of tissue in contact with the septa.

External Temperature Change Implementation

In some embodiments, the temperature rise in connective tissue (e.g., fascia and/or septa) is implemented in an external manner. External heating can heat the whole subcutaneous region, a portion of the subcutaneous region, and/or selectively heat the fascia and/or the septa within the region. In another embodiment, external heating heats a portion of tissue in contact with the fascia and/or the septa. The external temperature rise can be accomplished externally using optical energy with wavelengths of from about 600 nm to 2300 nm or from about 900 nm to about 1850 nm. In another embodiment, microwave energy can be externally applied to the body of a subject; the microwave energy can have a power level suited to raise the temperature of a subcutaneous region and/or the connective tissue (e.g., the fascia and/or the septa) to from about 37° C. to about 100° C., or from about 38° C. to about 60° C., from about 44° C. to about 60° C., or from about 45° C. to about 50° C. or more generally to a temperature that is less than the temperature at which the connective tissue being treated becomes fully coagulated. A suitable power level can range from about 1 watt to about 100 watts or from about 10 watts to about 60 watts. In another embodiment, radio frequency energy (RF energy) can be externally applied to the body of a subject, the RF energy having a power level suited to raise the temperature of a subcutaneous region and/or the targeted connective tissue (e.g., the fascia and/or the septa) to from about 37° C. to about 100° C., or from about 38° C. to about 50° C., or from 45° C. to about 60° C., or from about 44° C. to about 50° C. A suitable power level can range from about 1 watt to about 100 watts or from about 10 watts to about 60 watts. In another embodiment, ultrasound energy (US energy) can be externally applied to the body of a subject, the US energy having a power level suited to raising the temperature of a subcutaneous region and/or the targeted connective tissue (e.g., the fascia and/or the septa) to from about 37° C. to about 100° C., or from about 38° C. to about 50° C., or from 45° C. to about 60° C., or from about 44° C. to about 50° C., for example. A suitable power level can range from about 1 watt to about 100 watts or from about 10 watts to about 60 watts.

In another embodiment, a subcutaneous region and/or the targeted connective tissue (e.g., the fascia and/or the septa) are heated via thermal conduction from the surface of the subject's body (i.e., from the patient's skin) using a hot plate. In some embodiments, one or more of optical energy, microwave energy, RF energy, ultrasound energy, and thermal conduction can be combined with surface cooling to protect the skin (e.g., the epidermis and the dermis) from overheating. Surface cooling methodologies can include contacting the skin surface with a cold gel plate, spray cooling, cold liquid or gas flow cooling, for example. Generally, the cooling medium that contacts the surface of the skin should have a temperature of from about −10° C. to about 20° C., more specifically, a sapphire cooling plate may have a temperature that falls within the range of from about −5° C. to about 10° C.

Methods that can be employed to selectively heat fascia, and/or septa include optical energy employed for selective absorption of subcutaneous tissue (e.g., fat tissue) in preference to skin tissue at suitable wavelength(s). Suitable wavelengths include wavelengths of about 915 nm, about 1208 nm, and about 1715 nm, because these wavelengths provide peak absorption of lipid(s), which is desirable when treating the fat contained (e.g., the lipids) in subcutaneous tissue in preference to skin tissue. Other methods that can be employed include employing microwave energy, US energy, and/or RF energy by selective current through septa due to the relatively low electrical impedance of connective tissue (e.g., fascia and/or septa) compared to surrounding lipid rich tissue.

Stretching of the Septa

The septa and/or the region of tissue including the septa are heated to a temperature in the range of from about 37° C. to about 100° C., or from about 38° C. to about 50° C., or from about 44° C. to about 60° C., or and from about 45° C. to about 50° C. and simultaneously with and/or subsequent to heating a stretching action is applied to the septa for a period of time necessary to maintain a substantially lasting, durable and/or irreversible extension of the septa. The period of time over which the stretching action can be applied can range from about a tenth of a second to about 24 hours, from about a tenth of a second to about 1 second, from about 30 seconds to about 24 hours, or from about 1 minute to about 1 hour or from about 10 minutes to about 30 minutes.

The temperature to which the connective tissue is heated and the time that the connective tissue is exposed to the temperature should be selected to avoid full or complete coagulation of the connective tissue. In one embodiment, the septa and/or region of tissue including the septa are heated to a temperature of about 45° C. or greater and the septa and/or the region of tissue including septa are stretched for a period of time of about 1 minute or greater.

Adipose tissue (i.e., fat tissue) in the region of cellulite has a relatively high heat capacity and a relatively low thermal conductivity compared to skin tissue and has a relatively large volume compared to other types of tissue, for example, skin tissue. Because adipose tissue has a relatively high heat capacity and a relatively large volume after exposure to a temperature increase, adipose tissue in the region of cellulite holds the increased temperature for a period of time that enables stretching to occur over a period of time after the heat source has been applied for example for up to about 1 hour. It is conceivable that heat applied internally (i.e., via heated tumescent solution having a temperature of up to 60° C. and ranging from about 40° C. to about 60° C. can raise the temperature of the septa and/or the fascia to from about 44° C. to about 60° C.) can hold the heat for a period of time that enables internal and/or external stretching to be applied for a period of up to about one hour after injecting the tumescent into the subject's body.

Stretching can be applied to the septa by any of a number of methods or means. For example, in one embodiment, suction is applied to the external surface of a portion of the skin via a vacuum applicator that suctions a portion of the skin thereby placing the skin under negative pressure. In another embodiment, stretching is applied by pushing fluid (e.g., liquid and/or gas) into the tissue in the region to be treated. Optionally, the fluid extends the tissue in the region to be treated by increasing the volume of the region of tissue to be treated by a factor of from about 10% to about 500%, or from about 20% to about 200%, or from about 50% to about 100%. In some embodiments, the fluid is pushed directly into the tissue in the region to be treated. Optionally, in some embodiments, a balloon or bladder in inserted in the region to be treated and is placed, for example, under the skin and/or above the muscle to accept the fluid and to hold the expanded shape for the desired period of time. Fluid can be inserted into the balloon and/or the bladder via injection. Once stretching is completed, the balloon and/or bladder can be deflated by, for example, removing the fluid using the device previously used to inject the fluid into the bladder. In some embodiments, once the balloon and/or the bladder are deflated the balloon and/or the bladder can be removed from the region to be treated. In one embodiment, the balloon and/or the bladder are inserted through an incision made in the subject's body, likewise, the balloon and/or the bladder may be removed via the same incision (e.g., the incision through which the balloon and/or the bladder were placed inside the subject's body).

Referring again to FIG. 1A the fat tissue 1006 includes adipose cells with lipid droplets 1016*a* that have extracellular space 1005 between lipid droplets 1016*a*. FIG. 1A shows that in tissue the adipose cells with lipid droplets 1016*a* are closely packed such that there is a relatively small amount of extracellular space 1005 in the fat tissue.

FIG. 1B shows the region of cellulite tissue discussed in relation to FIG. 1A being stretched. Such stretching of tissue in a region having the appearance of cellulite can be accomplished by external means, such as the devices disclosed in association with FIGS. 4, 5, 6A and 6B or by internal means, for example, by introducing fluid internally to the subject's body.

In one embodiment, FIG. 1B depicts a region of cellulite tissue after tumescent fluid has been injected inside the subject's body 1002 in the region of cellulite.

The quantity of tumescent fluid increases the volume of the region of cellulite in the subject's body by from about 10% to about 500%, or from about 20% to about 200%, or from about 50% to about 100%, or from about 25% to about 75%, or from about 35% to about 50%, or by about 100%. Thus, the tumescent fluid substantially increases the size of the subcutaneous region. Referring to the fat tissue 1006 shown in FIG. 1B, introduction of the tumescent fluid into the subject's body increases the extracellular space 1005 such that the adipose cells with the lipid droplets 1016*a* of the fat tissue 1006 are no longer as closely packed as they were prior to introduction of the tumescent fluid (as is depicted in FIG. 1A). Introduction of the tumescent fluid extends and/or stretches the skin (epidermis 1010 and dermis 1008) due to the increase in volume provided by the introduction of tumescent fluid to the tissue. In addition, the introduction of the tumescent fluid increases the length of the septa 1007*a* and 1007*b* while decreasing the septa thickness. Stretching the tissue region having cellulite by external means would result in a similar increase in the extracellular space 1005 between the lipid droplets 1006*a* of the fat tissue 1006 and in a similar lengthening of the septa 1007*a* and 1007*b*.

In order to maintain the elongated length of the septa 1007*a* and 1007*b* for a substantially lasting, durable and/or irreversible period of time, the temperature of the septa 1007*a* and 1007*b* must be increased so that it ranges from about 37° C. to about 100° C., or from about 38° C. to about 60° C., from about 44° C. to about 60° C., or from about 45° C. to about 50° C., Such a temperature increase in the septa can be accomplished by external means such as the devices disclosed in association with FIGS. 4, 5, 6A and 6B.

In some embodiments, the tumescent solution is preheated such that upon injection into the subject's body 1000 the preheated tumescent solution heats the tissue in the region of the septa 1007 to have a temperature of from about 44° C. to about 60° C., or from about 37° C. to about 50° C., or from about 38° C. to about 42° C. The pre-heated tumescent solution has a temperature of up to 60° C. and ranging from about 40° C. to about 60° C. in order to raise the temperature of the septa and/or the fascia to from about 44° C. to about 60° C.).

In other embodiments, the tissue region is stretched (e.g., by external means and/or by unheated tumescent solution) and the septa 1007 are heated by external means such as, for example, by applying ultrasound energy and/or laser or light energy to the region of tissue including the fascia and/or the septa themselves. The temperature of the septa 1007 and the period of time of stretching of the septa 1007 in the presence of the temperature increase are selected to achieve substantially lasting, durable and/or irreversible elongation of the septa 1007 to the length depicted in FIG. 1B. In order to maintain the elongated length of the septa 1007*a* and 1007*b* for a substantially lasting, durable and/or irreversible period of time, the temperature of the septa 1007*a* and 1007*b* must be increased so that it ranges from about 37° C. to about 100° C., or from about 38° C. to about 60° C., from about 44° C. to about 60° C., or from about 45° C. to about 50° C. The one or more energy sources employed to increase the connective tissue temperature can have a power level of from about 1 watt to about 100 watts, or from about 10 watts to about 60 watts. Once the connective tissue temperature is increased, the stretching action can be applied to the tissue region for a period of time that can range from about a tenth of a second to about 24 hours, from about a tenth of a second to about 1 second, from about 30 seconds to about 24 hours, or from about 1 minute to about 1 hour or from about 10 minutes to about 30 minutes. For example, the stretching action can be applied to the tissue region by the tumescent solution by maintaining the tumescent solution in the subject's body in the presence of the temperature increase for the desired time period (e.g., the time period necessary to achieve lasting elongation of the septa).

FIG. 1C shows the region of cellulite tissue discussed in relation to FIG. 1B after removal of the stretching force (e.g., removal of an external stretching force such as a vacuum and/or removal of an internal stretching force such as the tumescent solution). The septa 1007*a* and 1007*b* shown in FIG. 1C are elongated as a result of the stretching and exposure of increased temperature discussed in relation to FIG. 1B. As a result, the septa 1007*a* and 1007*b* shown in FIG. 1C enjoy a decrease of tension in the substantially vertical septa 1007 as compared to the septa 1007 shown in FIG. 1A prior to exposure to stretching and temperature increase. Exposing the septa 1007 to stretching and increased temperature provides an improved appearance of cellulite on the external surface 1004 of the female subject's body 1000.

Referring now to FIG. 2A the fat tissue 3006 includes adipose cells with lipid droplets 3016*a* that have extracellular space 3005 between lipid droplets 3016*a*. FIG. 2A shows that in tissue the adipose cells with lipid droplets 3016*a* are closely packed such that there is a relatively small amount of extracellular space 3005 in the fat tissue 3006.

Figure 2B:
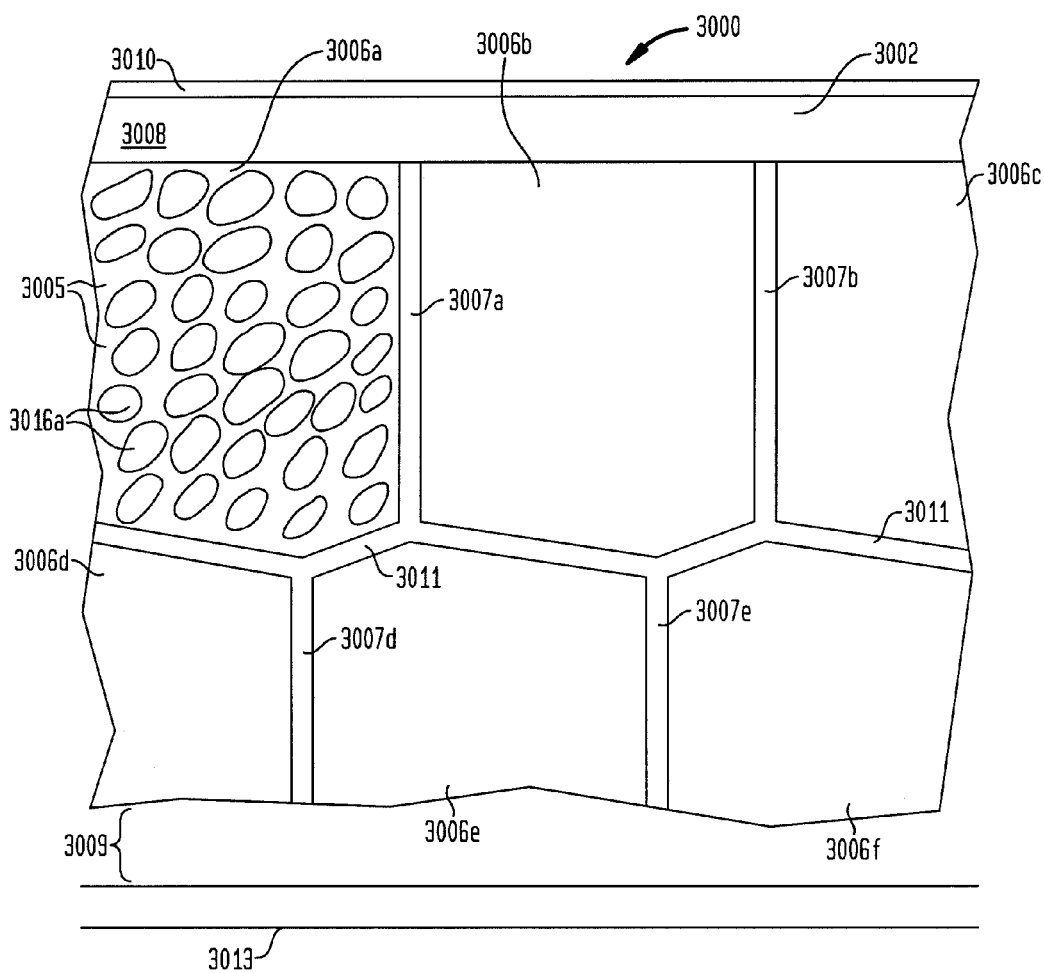
FIG. 2B is a schematic view of the inside of a female subject's body of FIG. 2A where the region of tissue is stretched (by an external device or by the addition of tumescent fluid, which is injected inside the female subject's body) to increase the volume of the subcutaneous tissue region thereby enabling connective tissue (e.g., septa and fascia) in the subcutaneous tissue region to be stretched in a manner that is substantially lasting, durable and/or irreversible.

FIG. 2B shows the region of cellulite tissue discussed in relation to FIG. 2A after the region of cellulite tissue has been stretched (e.g., by external means or by internal means such as injection of tumescent fluid inside the subject's body 3002 in the region of cellulite).

Still referring to FIG. 2B, in an embodiment where the tumescent fluid is injected to increase the volume of the region to be treated in the subject's body the tumescent fluid increased the volume of the region of tissue to be treated by a factor of from about 10% to about 500%, or from about 20% to about 200%, or from about 50% to about 100%, or from about 25% to about 75%, or from about 35% to about 50%, or by about 100%. Thus, the tumescent fluid substantially increases the size of the subcutaneous region. Referring to the fat tissue 3006 shown in FIG. 1B, introduction of the tumescent fluid into the subject's body increases the extracellular space 3005 such that the adipose cells with the lipid droplets 3016a of the fat tissue 3006 are no longer as closely packed as they were prior to introduction of the tumescent fluid (as is depicted in FIG. 2A).

Introduction of the tumescent fluid extends and/or stretches the skin (epidermis 3010 and dermis 3008) due to the increase in volume provided by the introduction of tumescent fluid to the tissue. In addition, the introduction of the tumescent fluid increases the length of the septa 3007a, 3007b, 3007d, and 3007e, which increases the length of the septa 3007 and increases the length of the fascia 3011 while decreasing the septa 3007 thickness and decreasing the fascia 3011 thickness. Stretching the tissue region having cellulite by external means would result in a similar increase in the extracellular space 3005 between the lipid droplets 3016a of the fat tissue 3006, a similar lengthening of the septa 3007a, 3007b. 3007d, and 3007e and in a similar lengthening of the fascia 3011 as described when stretching was accomplished by introduction of the tumescent fluid in the subject's body.

Referring still to FIG. 2B, in order to maintain the elongated length of the septa and/or the fascia for a substantially lasting, durable and/or irreversible period of time, the temperature of the septa 3007 and/or the fascia 3011 must be increased so that it ranges from about 37° C. to about 100° C., or from about 38° C. to about 60° C., from about 44° C. to about 60° C., or from about 45° C. to about 50° C. In some embodiments, tumescent solution is preheated such that the preheated tumescent solution has a temperature of up to 60° C. and a temperature that ranges from about 40° C. to about 60° C. such that upon injection into the subject's body 3000 the preheated tumescent solution heats the tissue in the region of the septa 3007 and/or the tissue in the region of the fascia 3011 to have a temperature of from about 44° C. to about 60° C., or from about 37° C. to about 50° C., or from about 38° C. to about 42° C.

In other embodiments, the tissue region is stretched (e.g., by external means and/or by unheated tumescent solution) and the connective tissue (e.g., the septa 3007 and/or the fascia 3011) are heated by an energy source provided by external means such as, for example, by applying ultrasound energy and/or laser or light energy to the region of tissue including the septa, the septa themselves, the region of tissue including the fascia and/or the fascia itself. The temperature of the septa 3007 and/or the fascia 3011 and the period of time of stretching of the septa 3007 and/or the fascia 3011 are selected to achieve substantially lasting, durable and/or irreversible elongation of the connective tissue (e.g., the septa 3007 and/or the fascia 3011) to the length depicted in FIG. 2B. The connective tissue to be treated (e.g., the septa and/or the fascia) is treated to reach a temperature below the temperature of full coagulation for example, from about 37° C. to about 100° C., or from about 38° C. to about 60° C., from about 44° C. to about 60° C., or from about 45° C. to about 50° C.

Once the connective tissue temperature is increased in the presence of a stretching force the temperature increase is held for a period of time that can range from about a tenth of a second to about 24 hours, from about a tenth of a second to about 1 second, from about 30 seconds to about 24 hours, or from about 1 minute to about 1 hour, or from about 10 minutes to about 30 minutes. The external energy sources employed to increase the connective tissue temperature can have a power level of from about 1 watt to about 100 watts, or from about 10 watts to about 60 watts.

FIG. 2C shows the region of cellulite tissue discussed in relation to FIGS. 2A and 2B after removal of the stretching force (e.g., removal of an external stretching force such as a vacuum and/or removal of an internal stretching force such as the tumescent solution).

FIG. 2C shows that the septa 3007 and fascia 3011 are elongated as a result of the stretching and exposure to the increased temperature discussed in relation to FIG. 2B. As a result, the septa 3007 and fascia 3011 shown in FIG. 2C enjoy a decrease of tension in the substantially vertical septa 3007 as compared to the septa 3007 shown in FIG. 2A prior to exposure to stretching and temperature increase. Likewise, exposure to stretching and increased temperature reduces the tension in the fascia 3011 by, for example, elongating at least a portion of the fascia 3011. Exposing the septa 3007 and the fascia 3011 to stretching and increased temperature provides an improved appearance of cellulite on the external surface 3004 of the female subject's body 3000.

In some embodiments, in order to avoid the muscle (e.g., the muscle underlying the fascia and/or the septa to be treated) from moving and/or pulling as a result of exposure to a stretching mechanism the practitioner can instruct the subject to flex their muscle in the treatment region. Flexing the muscle can aid in fixing the muscle and help prevent the muscle from being suctioned as well. In one embodiment, a flexing action can be accomplished in a desired muscle by using electrical conduction to fixate the muscle during application of an external stretching technique (e.g., by applying electrical muscle stimulation to the muscle beneath the area being treated to contract the muscle). The muscle can be stretched prior to, simultaneous with and/or subsequent with use of a stretching mechanism (e.g., an external stretching mechanism such as an external vacuum).

In one embodiment, during stretching, ultrasound energy is delivered to the septa. Ultrasound energy can support the substantially permanent expansion (i.e., stretching) of the septa by creating cavitation bubbles in the fiber of the septa. Cavitation bubbles in the fiber of the septa can weaken the septa to promote stretching. Ultrasound energy can be applied to generate one or more acoustic shock wave(s) that propagate through the dermis and the subcutaneous region to reach the septa. Ultrasound energy can be applied to generate oscillation of septa and oscillation of septa can support lasting (e.g., irreversible) elongation of the septa. In some embodiments the ultrasound frequency is selected to match or to substantially match the resonance frequency of oscillation of the septa and/or of the septa and any subcomponents that the septa contain. The resonance frequency of oscillation can range from about 10 MHz to about 1 GHz. In other embodiments, the ultrasound frequency is selected to match or to substantially match harmonics of the resonance frequency of the septa and any subcomponents that the septa contain. The harmonics of the resonance frequency can range from about 20 MHz to about 2 GHz.

In one embodiment, stretching is combined with vibration (e.g., vacuum is externally applied to the subject's skin together with a vibration action). In another embodiment, stretching is combined with torquing (e.g., twisting) of tissue, for example, vacuum is externally applied to the subject's skin together with a twisting action. The twisting action can have a torque that ranges from about 0.3 N-m to about 3 N-m. The vibration action can have a frequency that ranges from about 5 Hz to about 200 Hz.

Referring again to FIGS. 1A and 2A, the practitioner can be visually guided by the dimples 1003, 3003 on the subject's body 1000, 3000 to determine the region for treatment in an internal portion of the body 1002, 3002. In one embodiment, a handpiece including an aiming beam provides a visual aid to assist treatment of the subject. For example, where cellulite is being treated, a portion of the handpiece is inserted into the internal portion of the subject's body 1000, 3000. The practitioner can line the aiming beam of the handpiece in line with a visible dimple 1003, 3003 indicative of cellulite present on the external position of the body 1004, 3004. Once aligned with the visible dimple, with the aid of the aiming beam, the waveguide is positioned to treat the septa 1007 (e.g., to heat and/or stretch the septa) in the region of the visible dimple 1003. Alternatively, referring to FIG. 2A the waveguide is positioned to treat the septa 3007 and/or the fascia 3011 (e.g., to heat and/or stretch the septa and/or the fascia) in the region of the visible dimple 3003. In another embodiment, referring now to FIG. 1A, an aiming beam can be employed to locate individual septa (e.g., 1007*a*) in a region of skin. The aiming beam can make visible to the practitioner the presence of the septa 1007 in the subject's body 1000. Once the septa 1007 is made visible to the practitioner the septa 1007 and/or the region of the septa 1007 may be heated to a suitable temperature and simultaneous with or subsequent to heating the septa 1007 may be stretched by, for example, applying vacuum to the septa 1007.

In one embodiment, the treatment is combined with other visualization techniques that enable visualization of the connective tissue structure (e.g., the septa and/or fascia tissue structure) to control the location of the applicator and/or the results of the treatment. Suitable visualization techniques can include, for example, use of diagnostic ultrasound as a visualization technique.

In one embodiment, a cannula having a diameter that ranges from about 0.5 mm to about 8 mm, or about 2 mm is inserted into the body of a subject through an incision. The cannula includes an energy source (e.g., a light source) that heats the region of tissue into which the cannula has been inserted. The cannula and the energy source heat the region of tissue, which includes septa to a temperature of about 45° C. A source of vacuum is employed to stretch the connective tissue (e.g., the septa and/or the fascia tissue). The temperature of about 45° C. is employed because it avoids coagulation and it avoids melting of the adipose cells in the region of the connective tissue (e.g., the septa and/or the fascia tissue).

The desired level of connective tissue elongation may be confirmed via visual confirmation that the appearance of cellulite is reduced and/or eliminated. Where the treatment is non invasive (e.g., external treatment) the visual confirmation may be made just after treatment. Where the treatment is invasive (i.e., internal treatment with a cannula) the visual confirmation may likewise be made after the treatment is completed once the cannula is removed from the subject's body. Where the invasive treatment includes a fluid for example a liquid such as water or tumescent or a gas injected into the subject's body, the visual confirmation may be made upon release of the fluid (e.g., the tumescent or the gas). In some embodiments, the connective tissue that is elongated (e.g., the fascia and/or the septa) is increased in length by from about 5% to about 50%.

Figure 4:
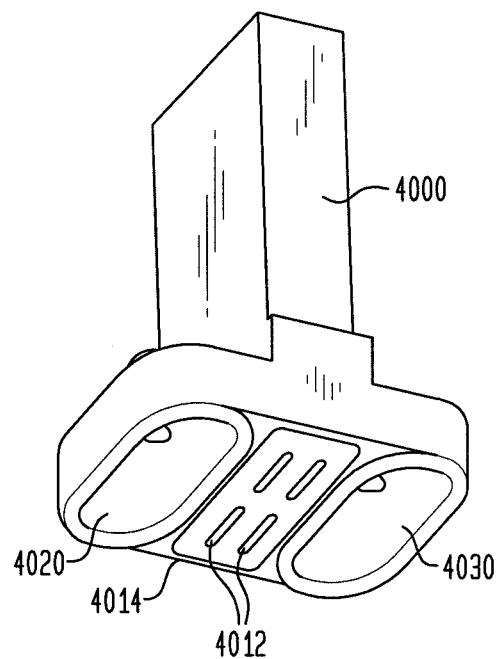
FIG. 4 shows a device for externally heating subcutaneous tissue including septa and/or fascia, the device includes a first vacuum, one or more energy source(s), a cooling plate, and a second vacuum.

FIG. 4 shows a device 4000 for externally heating a region of tissue, including septa, and for applying vacuum and/or suction to the region to stretch the heated septa. More specifically, the device includes a first vacuum 4020, one or more energy source 4012, a cooling plate 4014, and a second vacuum 4030. The device ensures good contact of the energy source 4012 by applying a first vacuum 4020 to a region of tissue prior to exposing the tissue to one or more energy source 4012 and, after heating of the tissue region is complete, a second vacuum 4030 is applied to the tissue region. In this way, the septa contained in the tissue region may be heated via the energy source 4012 and then stretched by a vacuum (e.g., 4020 or 4030). The vacuum pressure can range from about −500 mmHg to about −5 mmHg, or from about −350 mmHg to about −50 mmHg. The one or more energy source(s) 4012 may include one or more of the energy sources described herein (e.g., ultrasound, RF energy, light energy etc.). The power level of the energy source can range from about 1 watt to about 100 watts or from about 10 watts to about 60 watts. Where the energy source is light based the wavelength can range from about 600 nm to 2300 nm, or from about 900 nm to about 1850 nm. The cooling plate may include or incorporate any suitable cooling means known to the skilled person including, but not limited to, any of the cooling means disclosed herein. Generally, the cooling plate can have a temperature range of from about −5° C. to about 20° C. more specifically a sapphire cooling plate may have a temperature range of from about −5° C. to about 10° C. In this way the septa in the tissue region stretched in a manner that is substantially lasting, durable and/or irreversible. The device 4000 is employed on an external surface of the subject's body to improve the appearance of cellulite caused by substantially vertical and/or substantially tight septa and/or fascia in the tissue region.

Figure 5:
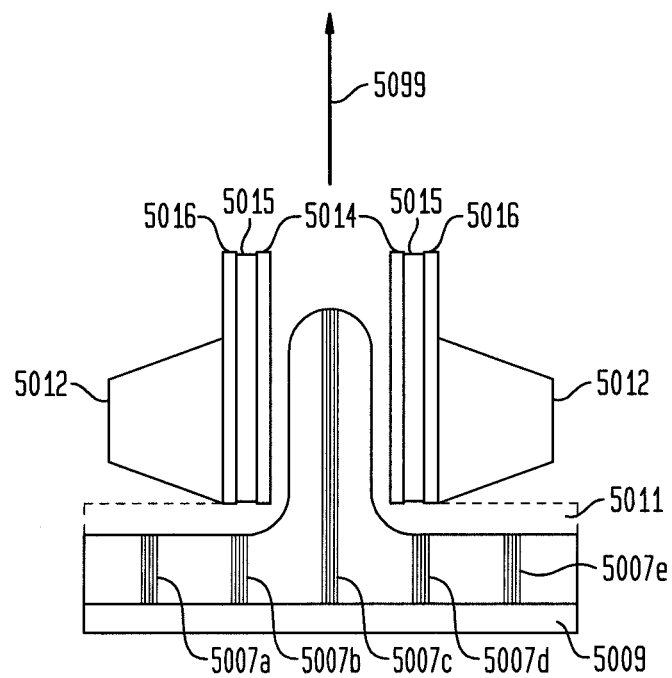
FIG. 5 shows a cross section of a device for externally heating a region of tissue, the device includes an energy source with adjacent cooling plate(s) and applies vacuum to the subcutaneous tissue including septa and/or fascia.

FIG. 5 shows a device for externally heating a region of tissue including septa 5007*a*-5007*e* disposed between skin tissue 5011 and muscle 5009. The device includes an energy source 5012 and adjacent the energy source 5012 are two cooling plates 5014 and 5016 that surround a cooling liquid 5015. The device also includes a source of vacuum 5099. The vacuum pressure can range from about −500 mmHg to about −5 mmHg, or from about −350 mmHg to about −50 mmHg. The vacuum source 5099 pulls the subject's tissue between the cooling plates 5014. The configuration of the device of FIG. 5 can create a "pinch" or a "fold" of tissue that is held adjacent the cooling plate 5014 of the device.

The cooling plate can be an optically transparent dielectric material. Generally, the cooling plate can have a temperature range of from about −5° C. to about 20° C. or the cooling plate can have a temperature range of from about −5° C. to about 10° C. The cooling plate may be made from sapphire. Cooling the plate to the temperature range of −5° C. to about 20° C. or from about −5° C. to about 10° C. allows deep heating by light without damaging the epidermis. Such cooling done in parallel with light delivery can allow irradiation times that can range from about a tenth of a second to about 24 hours, from about a tenth of a second to about 1 second, from about 30 seconds to about 24 hours, or from about 1 minute to about 1 hour or from about 10 minutes to about 30 minutes. In some embodiments, the treatment power density for wavelengths in the near-infrared wavelength range is on the order of from about 1 W/cm$^2$ to about 100 W/cm$^2$, or from about 1 W/cm$^2$ to about 10 W/cm$^2$. Heating and cooling may be cycled, cycling of heating and cooling can promote a substantially uniform temperature change in the area of tissue treatment. Thermocycling of heating and cooling can contribute to lasting elongation of connective tissue being treated (e.g., septa tissue and/or fascia tissue). Cycling of heating and cooling can be employed so that heating via the energy source and cooling have intensities that are matched to one another (e.g., as the energy for heating is increased the cooling temperature is decreased and as the energy for heating is decreased the cooling temperature is increased).

The energy source 5012 increases the temperature of the tissue region including the septa 5007. FIG. 5 depicts the energy source 5012 of the device applying energy to the tissue region, more specifically, to the septa 5007c in the tissue region while vacuum 5099 stretches the septa 5007c to which the energy source is being applied. In this way the septa 5007c is stretched in a manner that is substantially lasting, durable and/or irreversible. The vacuum 5099 may be modulated (e.g., the amount of suction may be alternated and/or modulated) to enhance stretching of the skin.

The device shown in FIG. 5 is employed on an external surface of the subject's body to improve the appearance of cellulite caused by substantially vertical and/or substantially tight septa 5007 and or by fascia (not shown in FIG. 5).

The power level of the energy source can range from about 1 watt to about 100 watts or from about 10 watts to about 60 watts. Where the energy source is a light based (e.g., laser) the wavelength can range from about 600 nm to 2300 nm or from about 900 nm to about 1850 nm.

The energy source 5012 can feature different optical schemes (i.e. with or without optical fibers) that can be used to irradiate the skin fold. In one embodiment, diode laser bars together with suitable optics are mounted in the device and create one or more irradiation areas (each having an irradiation area on the order of from about 5×20 mm$^2$, or from about 25×200 mm$^2$, or from about 15×70 mm$^2$) that are adjacent to the skin fold. In one embodiment, two diode laser bars (each having an irradiation area on the order of 15×70 mm$^2$) are located in the device each on one side of a skin fold. In another embodiment, diode light is delivered via beam-shaping optics through two cooled sapphire windows with one window located on each side of the skin fold (the cooled sapphire windows are on the order of 15×70 mm$^2$).

Referring still to FIG. 5 in an embodiment where the energy source 5012 includes ultrasound energy (e.g., acoustic energy), which may be applied to the region of tissue being treated at the same time as the stretching force is applied to the region of tissue being treated. In some embodiments, lasting stretching is enhanced by the acoustic energy whereby the fascia, septa, and/or all of the connective tissue in the treatment region vibrates in the presence of the acoustic energy.

More specifically, the device applies vacuum 5099 to a region of tissue to be treated (e.g., to a pinch of tissue) at least a portion of a side of the pinch of tissue is exposed to ultrasound energy (e.g., acoustic energy). Ultrasound energy (e.g., acoustic energy) may be employed as the only energy source 5012 and/or acoustic energy may be employed in combination with other sources of energy, such as, for example, light energy. Acoustic energy can provide mechanical vibration when the acoustic energy has a frequency range of from about 10 Hz to about 10 kHz. Acoustic energy can produce cavitation in the subcutaneous tissue when it has a frequency range of from about 5 kHz up to 1 MHz. Acoustic energy can achieve a heating effect when it has a frequency range from about 0.5 MHz to about 1 GHz. In one embodiment, a cooling element (e.g., a cooling plate 5014, 5016) contacts the skin surface while the acoustic and/or light energy is being applied to the skin surface. In one embodiment, the cooling element cools the skin surface down to, for example, 0° C. Suitable cooling elements may be made from, for example, cooled sapphire. Any suitable cooling mechanism may be employed such as, for example, a peltier cooler.

Figure 6A:
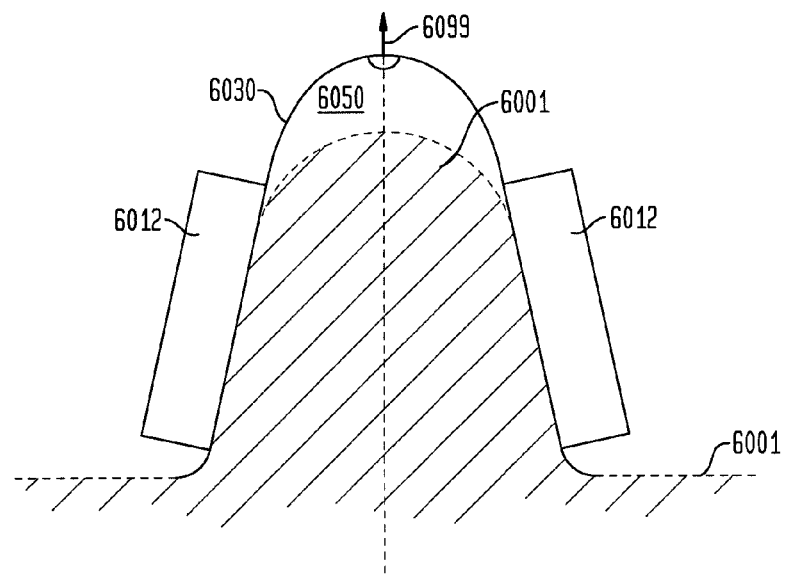
FIG. 6A shows a side view of a device having an outer housing which allows the recess in the device to accommodate varying tissue thicknesses (e.g., tissue fold thicknesses). The device features one or more energy source(s) and is adapted to apply vacuum pressure to the tissue region that is held within the device recess during treatment.
Figure 6B:
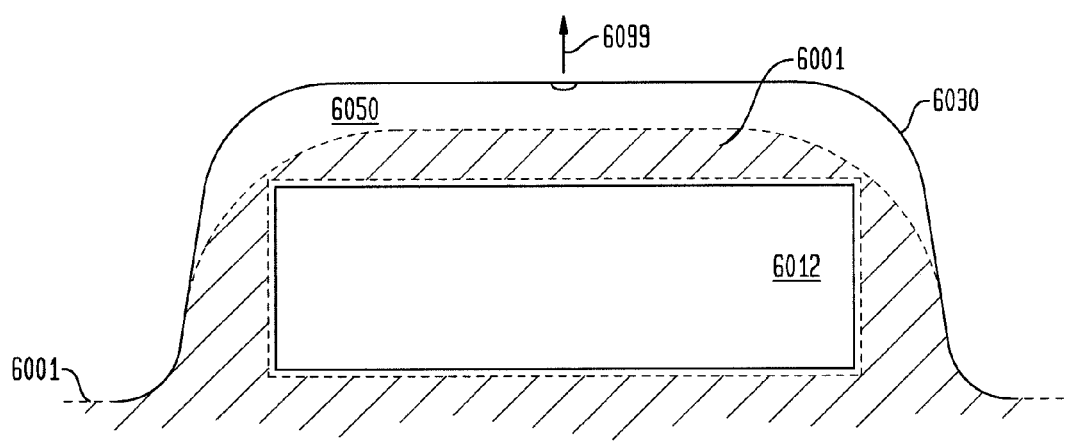
FIG. 6B shows a cross section of the device of FIG. 6A.

In one embodiment, referring to FIGS. 6A and 6B, the device has an outer housing 6030 that may be structurally flexible (made, for example, from silicone rubber), which allows the device to accommodate varying skin fold thicknesses. Alternatively, the outer housing 6030 can be made from a rigid material. In such a device the energy source(s) 6012 (e.g., optical component(s)) may be located on only a portion of the device. For example, in one embodiment, the device features two separate sapphire treatment windows 6012 that are separated from one another by the material of the outer housing 6030 (e.g., the flexible material of the outer housing) and vacuum 6099 is pulled through the device. A region of tissue to be treated 6001 includes skin and subcutaneous tissue, and during treatment within the recess 6050 of the device the region of tissue to be treated 6001 can assume the shape of a pinch or a fold when the region to be treated 6001 is pulled into the recess 6050 within the device. During use of the device, additional mechanical pressure can be applied to the energy source(s) 6012 (e.g., two sapphire treatment windows) to ensure good thermal/optical contact and to displace blood in the region of tissue to be treated. For example, in one embodiment, mechanical pressure such as a pushing or a squeezing force may be applied to the sapphire treatment windows 6012 that are disposed on or are adjacent to the flexible material of the outer housing 6030. Such a mechanical force may be employed on the device alternatively or in addition to application of a vacuum pressure 6099. In some embodiments, the skin fold is compressed and expanded (e.g., repeatedly compressed and expanded) to improve blood circulation during treatment of the tissue held within the device recess 6050 during treatment. The energy source 6012 may include one or more cooling element(s) employed to cool the region of skin tissue to be treated, suitable cooling elements can include the cooling plates disclosed in relation to FIG. 5. FIGS. 6A and 6B show the energy source(s) 6012 on the external surface of the outer housing 6030, however, suitable devices can include energy source(s) on the internal surface of the outer housing such that the energy source(s) directly contact the region to be treated 6001 when it enter the recess 6050 therein.

Optionally, the device includes vibration and/or massage. In one embodiment, massage is used in a twisting motion and/or a shearing motion provided in a direction parallel to the skin fold. In one embodiment, contact sensors are disposed on within the portion of the device in contact with the skin tissue and the contact sensors can be employed to ensure the skin being treated (e.g., a skin fold) stays in contact with the sapphire cooling windows. In one embodiment, a skin color sensor is employed to automatically adjust the power of the energy source (e.g., the diode laser) based on a measurement of the skin melanin optical density. In some embodiments, a temperature sensor is embedded in the device (e.g., in the sapphire window) and the temperature sensor can be employed to ensure that the skin does not overheat during treatment. The device may employ photon recycling to enhance heating of the skin fold by redirecting photons scattered out of the skin fold back into the skin fold. In other embodiments, one or more septa may be stretched by any of the means described herein and all or a portion of one or more septa may be cut and/or may fraction thereby to diminish and/or eliminate the tension in the septa that can cause the cellulite appearance. The one or more septa may be cut by any of the internal or external means described herein. Alternatively, the one or more septa may be cut by employing surgical tools known for cutting such as, for example, knives, scalpels, and/or cauterization devices.

The techniques described herein for improvement of cellulite appearance may be employed to treat the cellulite of subjects ranging in age from relatively young subjects that have just begun to exhibit the cellulite appearance (e.g., teenagers) or relatively older subject's including post menopausal and/or elderly female subjects.

What is claimed is:

1. A method of improving the appearance of cellulite, the method comprising:
    applying a stretching force to at least one of a septa tissue and a fascia tissue that is adjacent to fat tissue beneath a region of a subject's skin having the appearance of cellulite; and
    heating at least one of the septa tissue and the fascia tissue for a period of time and at a temperature in a range of about 38° C. to about 60° C. to achieve lasting elongation of at least one of the septa tissue and the fascia tissue upon release of the stretching force.

2. The method of claim 1 wherein applying the stretching force and heating at least one of the septa tissue and the fascia tissue occur simultaneously.

3. The method of claim 1 wherein the heating of at least one of the septa tissue and the fascia tissue occurs in the presence of the previously applied stretching force.

4. The method of claim 1 wherein applying the stretching force comprises inserting fluid into the subject's tissue.

5. The method of claim 4 wherein the fluid is pre-heated to heat at least one of the septa tissue and the fascia tissue.

6. The method of claim 1 wherein one or more of radiofrequency energy, ultrasound energy, light energy, and microwave energy are employed to heat at least one of the septa tissue and the fascia tissue.

7. The method of claim 1 further comprising utilizing a cannula to apply an energy source to heat at least one of the septa tissue and the fascia tissue.

8. The method of claim 7 wherein the cannula applies one or more of radiofrequency energy, ultrasound energy, light energy, and microwave energy to at least one of the septa tissue and the fascia tissue.

9. The method of claim 1 wherein vacuum pressure applies the stretching force.

10. The method of claim 1 wherein the temperature of at least one of the septa and the fascia range from about 44° C. to about 60° C.

11. The method of claim 1 wherein the temperature of at least one of the septa and the fascia range from about 40° C. to about 48° C.

12. The method of claim 1 wherein the period of time ranges from about 10 seconds to about 60 minutes.

13. The method of claim 1 wherein the period of time ranges from about 30 seconds to about 30 minutes.

14. The method of claim 1 further comprising cooling the external surface of the region of the subject's skin.

* * * * *